United States Patent [19]

Cho et al.

[11] Patent Number: 5,656,289
[45] Date of Patent: Aug. 12, 1997

[54] PHARMACEUTICAL FORMULATIONS THAT HAVE A BIOLOGICALLY ACTIVE HYDROPHILIC PHASE AND A CHYLOMICRA-CONTAINING HYDROPHOBIC PHASE

[75] Inventors: Young W. Cho, Chester, N.J.; Michael John Flynn, Surrey, England

[73] Assignee: Patralan Limited, Channel Islands, Great Britain

[21] Appl. No.: 207,236

[22] Filed: Feb. 16, 1994

Related U.S. Application Data

[63] Continuation of Ser. No. 61,505, May 14, 1993, abandoned, which is a continuation of Ser. No. 908,592, Jun. 30, 1992, abandoned, which is a continuation of Ser. No. 414,208, Sep. 29, 1989, abandoned.

[30] Foreign Application Priority Data

Sep. 29, 1988 [GB] United Kingdom ............... 8822857

[51] Int. Cl.⁶ .................. A61K 9/107; A61K 9/48; A61K 9/127
[52] U.S. Cl. .................. 424/455; 424/451; 424/456; 424/463; 424/450; 514/2; 514/3; 514/21; 514/866; 514/937; 514/938; 514/941; 514/943
[58] Field of Search .................. 424/450, 489, 424/499, 502, 435, 451, 455, 456, 464; 514/936–944, 2, 3, 21, 866

[56] References Cited

U.S. PATENT DOCUMENTS

| | | | |
|---|---|---|---|
| 4,146,499 | 3/1979 | Rosano | 252/186 |
| 4,165,385 | 8/1979 | Lefebvre | 424/363 |
| 4,536,324 | 8/1985 | Fujiwara et al. | 252/311 |
| 4,849,227 | 7/1989 | Cho | 424/463 X |
| 4,851,220 | 7/1989 | Yim | 514/937 |
| 4,855,090 | 8/1989 | Wallach | 424/450 X |

FOREIGN PATENT DOCUMENTS

| | | |
|---|---|---|
| 0 140 085 | 5/1985 | European Pat. Off. |
| 0 272 097 | 6/1988 | European Pat. Off. |
| 0 277 776 | 8/1988 | European Pat. Off. |
| 55-17328 | 2/1980 | Japan ............... A61K 9/10 |
| 57-72920A | 10/1980 | Japan. |
| 58-21622 | 2/1983 | Japan. |
| 0155109 | 8/1985 | Japan ............... 424/450 |
| 61-72721A | 4/1986 | Japan. |
| 2 085 729 | 5/1982 | United Kingdom. |
| 88/06881 | 9/1988 | WIPO. |
| 89/00812 | 2/1989 | WIPO. |

*Primary Examiner*—Gollamudi S. Kishore
*Attorney, Agent, or Firm*—Foley & Lardner

[57] ABSTRACT

Orally or rectally administrable formulations of biologically active material comprise a water-in-oil microemulsion, wherein the hydrophilic phase of the microemulsion comprises the biologically active material and the hydrophobic phase comprises chylomicra or material capable of forming chylomicra in the intestinal mucosa after administration. The biologically active material may be any of a wide range of substances including insulin, calcitonin and somatotrophin or growth hormone. Formulations of the invention are particularly suitable for the oral administration of insulin in the treatment of diabetes.

60 Claims, 3 Drawing Sheets

PHARMACEUTICAL FORMULATIONS THAT HAVE A BIOLOGICALLY ACTIVE HYDROPHILIC PHASE AND A CHYLOMICRA-CONTAINING HYDROPHOBIC PHASE

This application is a continuation, of application Ser. No. 08/061,505, filed on May 14, 1993, now abandoned, which is a continuation of Ser. No. 07/908,592, filed Jun. 30, 1992, now abandoned, which is a continuation of Ser. No. 07/414,208, filed Sep. 29, 1989 now abandoned.

This invention relates to pharmaceutical formulations. More particularly, the invention relates to orally or rectally administrable formulations of biological active material, particularly proteinaceous materials.

Medical practice has for many years prescribed or advised the administration of many biologically active materials for the treatment or prophylaxis of a wide variety of diseases or conditions. One of the most well known, but by no means the only, prescribed biologically active proteinaceous material is insulin, which is used for the control of diabetes.

Possibly the easiest method of taking any medication is oral ingestion. Such route of administration, which may be by means of syrup, elixir, tablets, capsules, granules, powders or any other convenient formulation, is generally simple and straightforward and is frequently the least inconvenient or unpleasant route of administration from the patient's point of view. It is therefore unfortunate, from the point of view of medical treatment and prophylaxis, that the preferred route of administration of proteinaceous medicaments and other biologically active materials involves passing the material through the stomach, which is a hostile environment for many materials, including proteins. As the acidic, hydrolytic and proteolytic environment of the stomach has evolved efficiently to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine.

The result, as many diabetics can testify, is that many proteinaceous medicaments have to be taken parenterally, often by subcutaneous, intramuscular or intravenous injection, with all the inconvenience, discomfort and difficulties of patient compliance that that entails.

This is not an isolated problem, as diseases needing control by the administration of proteinaceous material can be very widespread. Diabetes mellitus, for example, claims a large number of sufferers in many countries of the world. It is a chronic disorder affecting carbohydrate, fat and protein metabolism. It is characterised by hyperglycaemia and glycosuria, resulting from a defective or deficient insulin secretory response. Two major variants of the disease exist.

One variant, which is seen in about 10% of all idiopathic diabetics, is known as juvenile-onset diabetes or insulin-dependent diabetes mellitus ("IDDM"). This variant is frequently manifested for the first time in youth and is characterised by a progressive loss of insulin secretory function by beta cells of the pancreas and hence a progressive dependency on exogenous insulin for the maintenance of carbohydrate metabolism. This characteristic is shared by those non-idiopathic or "secondary" diabetics, whose disorders have their origin in pancreatic disease. The second variant of idiopathic diabetes mellitus is known as late-onset diabetes or non-insulin-dependent diabetes mellitus ("NIDDM").

Partly because of the large number of patients suffering from diabetes of one form or another, there is a need to develop oral formulations of insulin which are somehow protected against the hostile environment of the stomach. Although various prior attempts at developing such formulations have been made, the applicants are not aware of any prior composition that has to date been commercialised to any appreciable degree. Prior proposals of which the applicants are aware are as follows.

WO-A-8701035 relates to parenterally administrable formulations of fat-soluble drugs and vitamins; the formulations comprise 'pseudomicelles'.

WO-A-8705505 discloses orally ingestible compositions of insulin coated onto solid particles from an aqueous preparation; the insulin-coated particles are themselves then coated with lipid.

U.S. Pat. No. 4,849,405, published on 18th Jul. 1989, discloses orally ingestible compositions of insulin; the compositions are described as being two-phase preparations, and it appears that both phases are aqueous, with the phases effectively being kept separate by a coacervate system.

EP-A-0140085 discloses drug-containing lipid vesicle preparations.

Shichiri et al (*Acta diabet.lat.* 15 175–183 (1978)) disclose water-in-oil-in-water insulin micelles.

U.S. Pat. No. 4,784,845, published on 15th Nov. 1988, and U.S. Pat. No. 4,816,247, published on 28th Mar. 1989, disclose emulsion compositions for the parenteral administration of hydrophobic drugs.

JP-A-55017328 discloses water-in-oil-in-water emulsions containing insulin, for oral ingestion.

The present invention provides improved pharmaceutical formulations that can be delivered orally or rectally. More specifically, it has been discovered that even proteinaceous active agents hitherto administrable only parenterally can be given, via the more preferred oral or rectal route, as a component in a two-phase system that includes a hydrophobic phase containing chylomicra or material from which chylomicra are formed at the mucosal lining in vivo. Not only does the active agent appear to be bioavailable and bioactive but the efficiency of the delivery of the active material may be enhanced at least in some cases. Although the underlying basis for these effects is unclear, it is believed that a biologically active substance, when administered in association with chylomicra or the constituents of chylomicra, is targeted to the villae and microvillae of the intestinal wall, from where it is secreted into the lacteals and intestinal lymph and then drained into the thoracic duct and, ultimately, the circulating bloodstream.

According to a first aspect of the present invention, there is provided a pharmaceutical formulation comprising a microemulsion having a hydrophilic phase and a hydrophobic phase, wherein (A) the hydrophilic phase is dispersed in the hydrophobic phase, (B) the hydrophilic phase comprises a biologically active material and (C) the hydrophobic phase contains chylomicra or material from which chylomicra are formed in vivo. The hydrophilic phase can contain a physiologically compatible solvent for the biologically active material, such as water.

The invention therefore provides an orally or rectally administrable formulation of a biologically active material, the formulation comprising a water-in-oil microemulsion, wherein the aqueous or hydrophilic phase of the microemulsion comprises the biologically active material and the oil or hydrophobic phase comprises chylomicra or material capable of forming chylomicra in the intestinal mucosa after administration.

The biologically active material in formulations in accordance with the invention is absorbed. Orally administrable formulations are preferred but rectally administrable formulations may be appropriate in some circumstances.

Formulations in accordance with the invention therefore differ fundamentally from the prior art described above. The 'pseudomicelle' formulations of WO-A-8701035, although described as being similar to natural chylomicra, are not formulated to give an orally ingestible formulation. The active material would not, it appears, become biologically available if the formulation were to be ingested by mouth because of the lack of low HLB surfactant. The coated solid formulations of WO-A-8705505 do not form absorbable chylomicra, as again they do not contain a low HLB surfactant; with these formulations, the active ingredient is believed to be absorbed by pinocytosis. The formulations of U.S. Pat. No. 4,849,405 are aqueous and not true two phase (eg oil and water) systems, and so are completely different in character. None of this or the remaining prior art discussed above is believed to disclose compositions capable of forming chylomicra or administration.

The term "biologically active material" includes, in particular, pharmaceutically active proteinaceous materials. The proteinaceous material may be a pure protein, or it may comprise protein, in the way that a glycoprotein comprises both protein and sugar residues. The material may be useful in human or veterinary medicine, either by way of treatment or prophylaxis of diseases or their symptoms, or may be useful cosmetically or diagnostically. Examples of proteinaceous biological material which can be provided as orally or rectally administrable formulations in accordance with this invention include protein hormones such as insulin, calcitonin and growth hormone, whether from human or animals or semi- or totally synthetically prepared, erythropoietin, plasminogen activators and their precursors, such as t-PA, urokinase, pro-urokinase and streptokinase, interferons including human interferon alpha, interleukins including IL-1, IL-2, IL-3, IL-4 and IL-5 and blood factors including Factor VIII.

While it is not believed that there is any particular molecular size constraint on biologically active materials that can be formulated by means of the present invention, it will be apparent from the exemplary but non-limiting selection of biologically active materials given above that the invention is particularly suitable for formulating macromolecules. The molecular weight of such macromolecules may be about 1 kDa or above 5 kDa, about 10 kDa or above, or even about 15 kDa or above. Again, while it is not believed that hydrophilicity or hydrophobicity (lipophilicity) of the biologically active material is particularly critical, the invention readily enables hydrophilic molecules such as insulin, calcitonin (especially salmon calcitonin) and growth hormones or somatotrophin (especially porcine somatotrophin), all of which (particularly salmon calcitonin) are so hydrophilic as to be hygroscopic.

The amount of biologically active material present in a formulation of the invention will naturally depend on the nature of the material and will be such an amount as to make prescription of conveniently administrable amounts a practicable proposition. Bearing these considerations in mind, formulations in accordance with the invention may contain from 1 mcg, 10 mcg, 0.1 mg or 1 mg per liter to 1, 10 g or 100 g per liter.

Microemulsions are themselves known, particularly for formulating such simple organic molecules as herbicides. Like macroemulsions, microemulsions have two phases: a hydrophilic phase and a hydrophobic or lipophilic phase. It should be understood that, in this specification, the term "hydrophilic phase" should not be taken to mean that water is present to the exclusion of all other ingredients in that phase: rather, the phase is simply hydrophilic. Similarly, the term "hydrophobic phase" or "non-aqueous phase", should not be taken to mean that only an oil is present or, indeed, that that phase should contain any hydrocarbon material commonly known by the term "oil": rather, this phase will generally be a hydrophobic phase. Both phases, however, will generally be substantially liquid.

Characteristics of microemulsions include the droplet size and enhanced stability. Microemulsions have droplets sizes whose mean diameter is generally less than 10 microns and often less than 1 or 2 microns. In fact, some microemulsions can have average droplet sizes of 200 nm or less. The term "microemulsion" as used in this specification means any sufficiently stable two-phase system in which one phase is dispersed in the other. Certain two-phase systems sometimes classed as "emulsions" or "macroemulsions" may therefore fall within the scope of the term "microemulsions", as used herein. The droplet size of the substantially discontinuous dispersed phase may be less than 2 microns. Droplet size may be measured by scanning electron microscopy, by dark phase light microscopy, by conductivity measurements, by light (for example laser light) scattering or by any other convenient method. "Droplet" refers to the entities that make up the discontinuous phase.

The stability of microemulsions, as the term is used in this specification, is demonstrated by the fact that the microemulsions tend not to separate when left to stand; stability is "sufficient" if it allows for further processing, if desirable or necessary, and/or adequate shelf life. Furthermore, certain microemulsions can be translucent or transparent, often having a coloured tinge.

The volume:volume ratio of the hydrophilic phase:hydrophobic phase will generally be in the range of from 0.1:1 to 10:1, for example from 0.2:1 to 5:1, typically from 0.5:1 to 2:1.

The hydrophilic phase may contain a water miscible solvent, for example to aid in formulating. Ethanol or another suitable simple organic solvent may therefore be present. The nature of the solvent used will depend on the active material. The hydrophilic phase may be as water:solvent mix, for example in v/v proportions of 0.5:1 to 2:1.

It has been mentioned above that the hydrophobic phase either comprises chylomicra or material capable of forming chylomicra at the intestinal mucosa.

Chylomicra occur naturally as minute particles predominantly comprising fat, usually present in blood plasma, particularly after digestion of a fatty meal. Each chylomicron may be regarded as a protein-lipid complex, whose major lipid component comprises triglycerides, which has a density of about 0.95–1.006 and a flotation rate upon ultracentrifugation of more than 400. It generally comprises about 80 to 90%, more particularly 85 to 88%, mono-, di- and tri-glycerides; 5 to 19%, more particularly 6 to 9%, phospholipids; 1 to 3%, more particularly 2%, cholesterol esters; 0.1 to 2%, more particularly 1% free fatty acids; and 1 to 3%, more particularly less than 2%, protein. The protein components are apoproteins, in particular apoproteins A, B, C and E. It should be noted that to form chylomicra in the gut is not necessary to supply exogenously all the components, as some of them can be supplied by the body.

Chylomicra are formed at the mucosa of the intestinal wall during the absorption of triglycerides by animals. After the ingestion and hydrolysis of fatty acids to monoglycerides and their interaction with bile to form mixed micelles, the fatty acids and monoglycerides diffuse into the mucosa, wherein the fatty acids and monoglycerides derived from long chain triglycerides are re-esterified to triglycerides, which interact with cholesterol and phospholipids (both of which may be absorbed or newly synthesised). The resulting globule becomes encased in a protein coat (predominantly, apoprotein B) to result in chylomicra. Cholesterol ester, or cholesterol, is believed to act as a base or matrix for the other non-protein components of the chylomicra. The chylomicron bypasses the liver and is secreted through the lymphatic vessels into the thoracic duct to the circulating blood system.

Chylomicra may be precipitated from human, porcine or bovine serum with vinyl polymers, e.g. polyvinylpyrrolidone (PVP), extracted from the lymph fluid in the thoracic duct, or prepared synthetically. For example, when prepared from fresh human, porcine or bovine serum, to every 10 ml of fresh serum at least 1.25 g of NaCl is 2.5 ml PVP are added, and the mixture is centrifuged at 2500 rpm for 30 minutes. The resulting supernatant contains PVP-chylomicron complex.

Alternatively, chylomicra may be obtained from anaesthetised, fasting pigs by placing trachael and gastric tubes under general anaesthesia, and cannulating the thoracic duct with a polyethylene catheter. About 250 g of cream are forced into the animal's stomach through the gastric tube every three hours, and the lymph fluid is collected into a beaker at 4° C., while a physiological saline solution is infused through a cannulated vein. After collecting the lymph fluids for 12 to 18 hours from the cannulated thoracic duct, the collected lymph fluid is diluted with twice the volume of 0.9% NaCl solution and centrifuged at 25,000 g for 3 hours at 4° C. To the supernatant chylomicron solution, one half of the initially diluted volume of 0.9% NaCl is added, and kept in the cold (4° C.) until used (modified from Sagami et al: *Protein, Nucleic Acid, Enzymes* (Japanese), 10: 443, 1965).

As an alternative to chylomicra, the hydrophobic phase can comprise material which forms chylomicra at the intestinal mucosa. Such material comprises, at its broadest:

cholesterol or any other material that forms a chylomicron matrix;

lecithin or any other useful phospholipid; and a lipophilic surfactant, such as a long chain (for example $C_{16}$ to $C_{24}$ saturated or unsaturated) fatty acid, optionally esterified as a glycerol ester, which may be a mono-, di- or tri-glyceride.

As an optional additional component, a suitable cholesterol ester (e.g. formed from a long chain fatty acid) may be present. As an alternative to lecithin (which is the trivial name for phosphatidyl choline), other phosphatidyl amino acids such as phosphatidyl ethanolamine (cephalin), phosphatidyl serine or phosphatidyl inositol may be used. Phosphatidyl glycerol derivatives such as phosphatidyl glycerol itself, 3'-O-lysylphosphatidyl glycerol and diphosphatidyl glycerol (cardiolipin) may be other suitable alternatives. Of course, mixtures of phospholipids may be used. As the lipophilic surfactant it is preferred to use fatty acid or acids optionally esterified to form glycerides; they will preferably be $C_{18}$ to $C_{24}$ saturated or unsaturated acids such as oleic acid, linoleic acid, linolenic acid or some other suitable acid. Although apoproteins may be added to the chylomicra forming material, their presence is not obligatory. Chylomicra can be formed in vivo even if apoproteins are not added to the chylomicra-forming materials; although the applicants do not wish to be bound by this theory, it seems likely that apoproteins are either already available or synthesised de novo for use when the chylomicra-forming materials are present.

It is readily possible to determine by simple, but not undue, experimentation whether a formulation putatively in accordance with the invention has for its hydrophobic phase material capable of forming chylomicra in the intestinal mucosa after administration. The determination may be carried out by infusing the formulation under test into the duodenum of a pig and monitoring insulin (or other biologically active material) levels in the lymph fluid, hepatic portal blood and peripheral venous blood. A significant elevation of insulin in the lymph fluid, and not in the hepatic portal blood, confirms that the active material is absorbed through the lymphatic system, and not via the portal vein. The level of insulin in the lymph fluid may be twice, five times, ten times, fifty times or even a hundred times higher than in the hepatic portal blood. A detailed protocol for such a determination is given in the examples, and may be followed exactly or with suitable modifications if appropriate.

A hydrophobic phase which is capable of forming chylomicra in the intestinal mucosa, as discussed above, contains as its minimum essential ingredients:

cholesterol or any other material that forms a chylomicron matrix;

lecithin or any other useful phospholipid; and a lipophilic surfactant.

In principle there are three ways in which materials may be absorbed through the intestinal membrane. Small hydrophilic, water-soluble chemicals such as sugar, are known to be absorbed through the "pore system" of the intestinal membrane, carried into the capillary circulation and then into the hepatic portal vein in man. Lipids and lipophilic substances, on the other hand, are known to be absorbed via two distinctively different mechanisms. Those fatty acids having relatively shorter carbon-chains (for example $C_2$–$C_6$ or $C_8$ acids such as caproic and caprilic acid) are absorbed through the intestinal membrane with enzymatic and physiochemical 'assistance' from bile salts and pancreatic lipase. Ultimately, such absorbed lower-chained fatty acids are drained into the capillary blood and carried into the hepatic portal vein. Those lipids and fatty acids having relatively longer chains, for example oleic acid and di-oleate and tri-oleate glycerides, as well as cholesterol and phospholipids, among other compounds which form chylomicrons within the membrane, are absorbed through the intestinal membrane wall by mechanisms which may not as yet be clearly understood. Once in the intestinal membrane, they participate in the formation of chylomicra and are then 'sucked' into the villae of the intestinal system, drained into the lymph fluid, collected the choracic duct and ultimately dumped into the systemic circulation.

Broad and preferred percentage compositions (which will generally be weight/weight percentages, but may be weight/volume or even volume/volume percentages) of the chylomicra-forming material for general purposes are given below, providing always that the total does not exceed 100%:

|  | Broad | Preferred |
| --- | --- | --- |
| Cholesterol (or other matrix) | 0.1–99.9 | 0.5–5 |
| Lecithin (or other phospholipid) | 0.1–99.9 | 0.5–10 |
| Lipophilic surfactant | 0.1–99.9 | 0.5–95 |
| Cholesterol ester | 0–10 | 0–5 |
| Non-esterified fatty acid | 0–75 | 0–50 |
| Apoprotein | 0–10 | 0–4 |

It has been determined that within these broad and preferred ranges, the hydrophobic phase may have certain preferred composition characteristics for certain biologically active materials. For example, for insulin (and also for interferons such as human interferons beta and gamma), the following narrower proportions (on the same basis and with the same proviso) are preferred:

|  | Broad | Preferred | Optimal |
|---|---|---|---|
| Cholesterol (or other matrix) | 0.5–5 | 0.5–2 | 1 |
| Lecithin (or other phospholipid) | 4–10 | 7–9 | 8 |
| Lipophilic surfactant | 50–95 | 80–90 | 86 |
| Cholesterol Ester | 0–5 | 0–4 | 3 |
| Non-esterified fatty acid | 0–2 | 0–1 | 0 |
| Apoprotein | 0–4 | 1–3 | 2 |

For salmon calcitonin (and also for erythropoietin), the following proportions (on the same basis and with the same proviso) are preferred:

|  | Broad | Preferred | Optimal |
|---|---|---|---|
| Cholesterol (or other matrix) | 0.5–5 | 1.5–4 | 2.7 |
| Lecithin (or other phospholipid) | 0.5–7 | 1.5–4 | 3.3 |
| Lipophilic surfactant | 0.5–5 | 1–3.5 | 2.4 |
| Cholesterol Ester | 0–5 | 0–1 | 0 |
| Non-esterified fatty acid | 0–45 | 1–35 | 21 |
| Apoprotein | 0–4 | 0–1 | 0 |
| For porcine somatotrophin (and also for tissue plasminogen activator and Factor VIII), the following proportions are preferred: | | | |
| Cholesterol (or other matrix) | 0.5–5 | 0.5–2 | 1 |
| Lecithin (or other phospholipid) | 5–40 | 10–25 | 16 |
| Lipophilic surfactant | 10–70 | 20–45 | 31 |
| Cholesterol Ester | 0–5 | 0–1 | 0 |
| Non-esterified fatty acid | 0–5 | 0–1 | 0 |
| Apoprotein | 0–5 | 0–1 | 0 |

Some hydrophobic-phase miscible organic solvent may be present, again possibly as an aid in formulation. The nature of the solvent will depend on the other materials present. Ethanol is often suitable. The amount of solvent may be, for example from 5 to 50% v/v, based on the volume of the oil phase.

To form microemulsions, it is sometimes necessary to use two different surfactants, one being hydrophilic and having a high hydrophile-lipophile balance (HLB), and the other being more lipophilic (as described above), and having a low HLB. The HLB value is a proportion of the hydrophilic group of the surfactant expressed as its weight percent of the surfactant molecule, divided by five. A totally hydrophilic molecule, such as polyethylene glycol, therefore has the theoretical maximum HLB value of 20.

Hydrophilic surfactants useful in the present invention, when present, have a very high HLB of at least 17 and possibly approaching 20. Lipophilic surfactants used in the invention have a low HLB of, for example, less than 10. Preferably, the lipophilic surfactant has an HLB value of less than 7 or even less than 4.

As general guidance it is preferred that each of the surfactants used in the preparation of formulations of this invention be selected from those surfactants classified as anionic or nonionic. These surfactants are particularly useful in pharmaceutical systems for their compatibility, stability, and non-toxicity. Surfactants generally suitable for the various purposes in the present invention include long chain ($C_{16}$ to $C_{24}$) fatty acids, e.g. palmitic acid, stearic acid and oleic acid; esters of long chain ($C_{16}$ to $C_{24}$) fatty acids, e.g. sodium palmitate, sodium stearate and sodium oleate; sodium lauryl sulphate; polyethylene glycol; polyethylene glycol alkyl ethers; fatty acid esters of polyethylene glycol, e.g. polyethylene glycol mono- or di-stearate; propylene glycol; fatty acid esters of propylene glycol, e.g. propylene glycol monostearate; glycerine; fatty acid mono- or polyglycerides, such as glyceryl monostearate; polyoxyethylene fatty acid esters, ethers and amines, e.g. polyoxyethylene mono- and di-stearate, and polyoxyethylene lauryl ether; polyoxyethylene sorbitan esters, e.g. polyoxyethylene sorbitan monolaurate, monopalmitate, monostearate or monooleate; polyoxyethylene alkyl phenols and alkyl phenyl ethers; polyoxyethylene castor oil; sorbitan fatty acid esters; the polysorbates; stearylamine; triethanolamine oleate; vegetable oils, e.g. sesame seed oil or corn oil; cholesterol; and tragacanth.

The surfactants of choice will of course be those which are currently on the approved list for pharmaceutical use and will have appropriately low $LD_{50}$ values. There follows a list of certain exemplary surfactants, together with their HLB values and, where known, their $LD_{50}$ values.

Examples of suitable high HLB surfactants are as follows:

| Chemical Identity | HLB | $LD_{50}$ g/kg |
|---|---|---|
| Polyethylene Glycol Esters | | |
| PEG-monostearate | 19.1 | ? |
| Polyoxyethylated Glycol Monoethers | | |
| POE(23) lauryl ether | 17.0 | 9 |
| Polyoxyethylated Fatty Acids | | |
| POE(40) lauric acid | 17.9 | ? |
| POE(100) lauric acid | 19.1 | ? |
| POE(40) oleic acid | 17.4 | ? |
| POE(100) oleic acid | 18.8 | ? |
| POE(40) stearic acid | 17.8 | ? |
| POE(50) stearic acid | 17.9 | >25 |
| POE(100) stearic acid | 18.8 | 25 |

| Chemical Identity | HLB | $LD_{50}$ g/kg |
|---|---|---|
| Glycerol Esters | | |
| Glycerol monooleate | 3.8 | ? |
| Polyoxyethylated Glycol Monoethers | | |
| POE(4) lauryl ether | 9.5 | 9 |
| POE(2) cetyl ether | 5.3 | 22 |
| POE(2) stearyl ether | 4.9 | >25 |
| POE(2) oleyl ether | 4.9 | 25 |
| Polyoxyethylated Fatty Acids | | |
| POE(4) lauric acid | 9.3 | ? |
| POE(4) oleic acid | 7.7 | ? |
| POE(4) stearic acid | 7.7 | ? |
| Sorbitan Fatty Acid Esters | | |
| Sorbitan monolaurate | 8.6 | 41 |
| Sorbitan monopalmitate | 6.7 | >16 |
| Sorbitan monostearate | 4.7 | 31 |
| Sorbitan tristearate | 2.1 | >16 |
| Sorbitan monooleate | 4.3 | >40 |
| Sorbitan sesquioleate | 3.7 | ? |
| Sorbitan trioleate | 1.8 | >40 |
| Sorbitan monoisostearate | 4.7 | ? |
| Polyoxyethylated Sorbitan Fatty Esters | | |
| POE(4) sorbitan monostearate | 9.6 | >40 |
| POE(5) sorbitan monooleate | 10.0 | >37 |

-continued

| Chemical Identity | HLB | LD$_{50}$ g/kg |
|---|---|---|
| Polyoxyethylated Castor Oils | | |
| POE(10) castor oil | 6.3 | ? |
| POE(10 hydrogenated castor oil | 6.3 | ? |
| Poloxamers | | |
| POE(7)-POP (17) (L42) | 8 | ? |
| POE(4)-POP (23) (L61) | 3 | ? |
| POE(10)-POP (23) (L62) | 7 | ? |
| POE(27)-POP (23) (L64) | 7 | ? |
| POE(6)-POP (30) (L81) | 2 | ? |
| POE(19)-POP (37) (L92) | 5.5 | ? |
| POE(8)-POP (43) (L101) | 1 | ? |
| POE(32)-POP (43) (P103) | 9 | ? |
| POE(10)-POP (53) (L121) | 0.5 | ? |

It should be noted that mixtures of surfactants can often be used in place of single surfactants in the present invention. For example, instead of a single hydrophilic surfactant, a mixture of two or more relatively hydrophilic surfactants could be used; the effective HLB of the mixture should, however, be greater than 17. By "effective HLB" is meant that the hydrophile-lipophile balance of the mixture of surfactants should be equivalent to a single surfactant having an HLB of greater than 17. Similarly, mixtures of lipophilic surfactants can be used in place of a single lipophilic surfactant. Again, the effective HLB of the lipophilic surfactants should be less than 10.

The choice of the amount of surfactant to be used in formulations of the present invention is left as a matter of choice to those skilled in the art. Naturally, precise amounts that will be optimal in each case will depend very much on the precise nature of the surfactants used and what other ingredients in the formulations are present. Nevertheless, as general guidance, the amount of hydrophilic surfactant, when present, will generally be in the range (based on the total volume of the formulation) of from 0.1 g to 50 g per liter, with a range of from 0.5 to 25 g per liter usually being preferred and from 1 g to 10 g per liter often being optimal. The lipophilic surfactant has been discussed above in relation to the oil phase of the microemulsion. It will generally be present in an amount of from 0.1 g to 100 g per liter, with a range of from 0.5 g to 50 g per liter being preferred and a range of from 2 g to 25 g per liter often being optimal, with the figures again being based on the total volume of the formulation.

While it is not essential for any other ingredients to be present, as a matter of practice, it is usually highly convenient for other ingredients to be added. One further component that is often highly desirable is a protease inhibitor, which may be in the form of one or more individual protease inhibitors. Protease inhibitors useful for the present invention can broadly be divided into two categories. First, there is the category of protease inhibitors which are useful in limiting or preventing the degradation of the biologically active material if it is proteinaceous. Such protease inhibitors should have the effect of inhibiting proteolytic enzymes found in the gastrointestinal tract, such as trypsin, chymotrypsin and carboxypeptidase. In the case of insulin, the protease inhibitors will generally be inhibitory of the class of enzymes that have come to be known as insulinase, which includes the enzyme trans-sulphatase. Suitable sources of trypsin inhibitors can be extracted from soy beans or egg white (ovomucoid). Secondly, if apoprotein is present in formulations in accordance with the invention, it is desirable to add protease inhibitors to reduce the amount of degradation of the apoprotein before it reaches the intestinal mucosa.

Generally speaking, similar protease inhibitors can be used as for the protection of proteinaceous biologically active materials, and so a single protease inhibitor may serve both functions. The choice of the amount of protease inhibitor to be added will be well within the skill of a person skilled in the art, but generally will be in amounts up to about 0.1% w/v, or even 0.5% w/v.

Another optional ingredient is a stabiliser for the biologically active material. The precise nature of the stabiliser, if present, will of course depend on the nature of the biologically active material itself. For example, there are a number of well defined stabilisers for insulin, which can be advantageously be incorporated in insulin-containing formulations in accordance with the invention. Examples include hydroxypropyl cellulose (HPC), calcium salts and citrate salts. Calcium is known not only to stabilise insulin but also to have an additional beneficial effect of increasing the porosity of cell membranes, thereby facilitating entry of the active material into the intestinal wall cells. The amount of stabiliser to be present will again depend on its nature and the nature of the biologically active material; the choice of the amount will be well within the capabilities of a person skilled in the art but will often be in amounts up to about 1 or 2% w/v.

Although formulations in accordance with the present invention are microemulsions, as defined in this specification, it can be desirable in some instances to incorporate emulsification aids, which may be conventional emulsification aids used in the preparation of macroemulsions. Some emulsification aids are surfactants, and surfactants useful for this purpose are not restricted to any particular HLB values. Useful emulsification aids include cholesterol, stearic acid, sodium stearate, palmitic acid, sodium palmitate, oleic acid, sodium oleate, glyceryl monostearate, polyoxyethylene 50 stearate, polyoxyethylene 40 stearate, polysorbate 20, polysorbate 40, polysorbate 60, polysorbate 80, propylene glycol diacetate, and propylene glycol monostearate.

The amount of emulsification aid to be present, if desired, will simply be enough to assist in adequately obtaining a stable microemulsion. The exact amount can be determined by a person skilled in the art; generally speaking they can be used in amounts of from 0 to 10% w/v, for example 0.1 to 5% w/v of the formulation as a whole.

If desired, one or more stabilisers and/or plasticisers may be added to formulations of the invention for even greater storage stability. As has been mentioned above, microemulsions tend not to separate on standing under normal conditions, but a greater degree of stability may be useful under some circumstances. Materials useful as stabiliser and/or plasticiser include dextrin, acacia, carboxypolymethylene and colloidal aluminium hydroxide. When stabilisers/plasticisers are added, they may be incorporated in amounts up to about 10% (w/v), preferably from about 0.5 to 6.5%, of the total preparation.

Formulations in accordance with the invention can contain various preservatives. Two particularly useful categories of preservatives are antioxidants and antimicrobial agents. Antioxidants are particularly useful because chylomicra and material capable of forming chylomicra (including apoproteins) are prone to degradation by autoxidation. Although this problem can be avoided by preparing formulations in accordance with the present invention under an inert atmosphere, such as nitrogen, this is a somewhat inconvenient and expensive process and so it is often preferred to add chemical anti-oxidants. Suitable pharmaceutically acceptable antioxidants include propyl gallate, butylated hydroxyanisole, butylated hydroxytoluene, ascorbic acid or sodium ascorbate, DL- or D- alpha tocopherol and DL- or D- alpha-tocopheryl acetate. The anti-oxidant, if present, may be added to formulations in accordance with the invention in an amount of up to, for example, 0.1% (w/v), preferably from 0.0001 to 0.3%.

Sesame oil, preferably as a refined chemical oil, may be added to formulations of the invention, as it has anti-oxidant activity. Sesame oil has the further advantage that it improves the flavour of the formulations (especially to oriental patients), thereby improving patient compliance. Sesame oil may be present in an amount of from 0.1 to 3% w/v preferably 5 to 20% w/v of the final liquid formulation. Other flavour enhancers, in appropriate amounts, may be present instead or as well.

Formulations in accordance with the present invention can be prepared and maintained under sterile conditions, and so avoid microbial contamination in this way. However, this is an extravagant procedure for an orally ingestible preparation, and so it would be more usual to include an antimicrobial preservative. Antimicrobial agents which may be used, generally in amounts of up to about 3% w/v, preferably from about 0.5 to 2.5%, of the total formulation, include methylparaben, ethylparaben, propylparaben, butylparaben, phenol, dehydroacetic acid, phenylethyl alcohol, sodium benzoate, sorbic acid, thymol, thimerosal, sodium dehydroacetate, benzyl alcohol, cresol, p-chloro-m-cresol, chlorobutanol, phenylmercuric acetate, phenylmercuric borate, phenylmercuric nitrate and benzylalkonium chloride.

Because of the inherent thermodynamic stability of microemulsions, liquid formulations in accordance with the invention can simply be prepared by mixing the aqueous and oil phases, which in turn can be prepared by mixing their respective ingredients together.

According to a second aspect of the invention, there is therefore provided a process for the preparation of an orally ingestible formulation in accordance with the first aspect, the process comprising admixing the ingredients.

Kinetic considerations, however, suggest that as a practical matter certain steps be taken to ensure the rapid and effective formation of microemulsion formulations in accordance with the invention. In particular, during or after the hydrophilic and hydrophobic phases have been added together, a microemulsion can be speedily formed by the use of a homogeniser such as an AUTOHOMOMIXER. (The word AUTOHOMOMIXER is a trade mark of Tokushu Kika, Tokyo.) The additional or alternative use of a microfluidiser may be advantageous.

Generally, it is preferred to add at least some (or at least one) of the components of the hydrophilic phase to at least some (or at least one, but preferably all) of the components of the hydrophobic phase with rapid mixing; and remaining components can be added appropriately.

One preferred process for the preparation of formulations of the invention containing both hydrophilic (high HLB) and lipophilic (low HLB) surfactants involves:

(a) rapidly mixing the biologically active material in a suitable aqueous solvent with the hydrophobic phase, which contains the low HLB surfactant;

(b) adding the high HLB surfactant with further rapid mixing; and (c) optionally coating a solid carrier with the formulation so formed.

Protease inhibitor may be added to the biologically active material before it is mixed with the hydrophobic phase. Antioxidant can be added before the rapid mixing of step (a). Stabiliser for the biologically active material can be added at the same time as the high HLB surfactant, as can further or alternative enzyme inhibitor(s).

It will be appreciated that, as formulations in accordance with the invention are microemulsions, they are likely to be liquid. However, liquid formulations may in some instances be less convenient than solid formulations, and so there are a number of ways in which formulations in accordance with the invention can either be made as or be converted into solid formulations. One way of preparing a solid formulation is simply to choose appropriate ingredients so that at storage temperatures the formulations in accordance with the invention are solid. Such preparations will generally revert to their liquid state at physiological temperatures, and therefore behave as liquids soon after being orally administered. However, this approach may not be convenient or indeed feasible in many cases. Therefore, if a solid formulation is desired, it is generally preferred to coat a liquid formulation in accordance with the invention onto a solid carrier, which may be in the form of granules or particles. (It should be noted that particles can be compounded into granules after coating.) The liquid formulation can be adsorbed onto or absorbed into the carrier. The carrier itself will for certain (particularly human) applications preferably be physiologically non-absorbable, and so will be excreted as faecal matter after having passed through the gastrointestinal tract. It is particularly useful to use, as a carrier, an agent which swells in the gastrointestinal tract (particularly the small intestine) such as by 10 to 200 times its volume. A rapidly expanding material is particularly preferred, and such materials include calcium carboxymethylcellulose, or hydroxypropylcellulose, sodium alginate, gelatin, cross-linked polyvinylpyrrolidone, "eruptible" rice and polystyrene.

A particularly suitable solid carrier including rapidly expanding material comprises: calcium carboxymethyl cellulose (eg 20 to 60% w/w, preferably 35 to 45% w/w); alginic acid or sodium alginate (eg 5 to 25% w/w, preferably 10 to 20% w/w); gelatin (eg 2 to 20% w/w, preferably 5 to 15% w/w), hydroxypropyl cellulose (eg 20 to 60% w/w, preferably 30 to 40% w/w) and sodium lauryl sulphate or another appropriate surfactant (eg 0.1 to 20% w/w, preferably 1 to 10% w/w). When these are the only ingredients, as is preferred, the percentage proportions will add up to 100%.

Particularly when used for veterinary applications, however, the carrier may be ingestible and may comprise a useful dietary component (for example a protein, carbohydrate, fat or mineral) for the animal being treated. Proteinaceous carriers are preferred in this instance, and oya bean powder is particularly suitable, as the formulation may conveniently be added to an animal's (eg a pig's) feed.

The liquid formulation can be coated onto the carrier in a variety of suitable ways, many of which will be well known in the art. Spray coating, for example in a fluidiser bed, is particularly suitable. The carrier will preferably be coated with from 50 to 500% of its weight with the liquid formulation.

Care has to be taken when spray coating a carrier with a liquid microemulsion formulation in accordance with the invention as described above. Because of the nature of the common components in the hydrophobic phase (cholesterol or other matrix, lecithin or other phospholipid and lipophilic surfactant), the temperature of the liquid formulation or the particles in the fluidiser bed must not be raised too high, otherwise the oil phase may become too free flowing. Conversely, if the temperature is allowed to drop too much, the formulation becomes too viscous to spray into the fluidised bed. Additionally, care has to be taken that the coated carrier particles do not cake excessively in the fluidiser.

Optimum results can be had by coating the carrier particles by the following processes, which themselves form part of the invention. According to one aspect of the invention there is provided a process for coating carrier particles with a liquid comprising a hydrophobe, the process comprising fluidising the carrier particles in a fluidiser bed, spraying the liquid onto the fluidised particles, heating the fluidising gas (which will usually be air) when the temperature in the fluidised bed is too low and cooling the fluidising gas when the temperature in the fluidised bed is too high. Fluidising gases have previously been heated, not least because fluidised bed spraying is conventionally carried out at about 80° C., and to use a cooled fluidising gas in situations such as this is against the accepted wisdom in the art.

By means of this aspect of the invention, the temperature in the fluidised bed can be kept within a suitable range. Exactly how large the range is, and what the limits of the range are, will obviously depend on the nature of the oil in the liquid being sprayed, and possibly the nature of the carrier particles and any other component(s) of the liquid and other parameters. When formulations in accordance with the first aspect are being sprayed, the temperature should be kept at 29° C.±5° C. preferably ±2° C., for best results. The invention also relates to apparatus for carrying at this aspect of the invention.

According to another aspect of the invention, there is provided a process for coating carrier particles with a liquid comprising an oil, the process comprising fluidising the carrier particles in a fluidiser bed and spraying the liquid into the fluidised particles, wherein the spraying is intermittent.

The time intervals between the spraying may be greater than the duration of the spray periods. Spray periods may be from 1 to 20 seconds, preferably from 2 to 15 seconds and typically from 5 to 10 seconds. Intervals between spraying may range from 5 seconds to 40 seconds, preferably 10 to 30 seconds and typically from 15 to 20 seconds.

It is particularly appropriate to combine this intermittent spray feature with the stabilised temperature feature mentioned above. Other preferred features of this process, as distinct from conventional spray drying include: occasional (eg every 1 to 10 seconds) pulsing the inside of the chamber of the fluidised bed apparatus with fluidising gas to dislodge particles which may have adhered to the chamber walls and/or to any filters which may be present; dehumidifying the fluidising gas (eg air); filtering the fluidising gas at least partially to remove oil or microbes or both; and/or providing rotating lump-breaking means rotating about an axis substantially at right angles to the direction of supply of fluidising gas, preferably without having a rotating mechanical agitator rotating parallel to the direction of supply of fluidising gas. The invention also relates to apparatus for carrying out this aspect.

In general terms it should be noted that the water content of the hydrophilic phase may be reduced or lost when solid carrier particles are spray coated. This does not remove the resulting formulation from the scope of the invention. The formulation may adequately rehydrate on administration.

Solid formulations in accordance with the invention may comprise pharmaceutically acceptable fillers and/or binders in appropriate amounts. Useful fillers include lactose, mannitol, calcium sulphate, dicalcium phosphate, tricalcium phosphate, and microcrystalline cellulose. Useful binders include acacia, tragacanth, gelatin, sodium alginate, ammonium calcium alginate, methylcellulose, sodium carboxymethylcellulose, ethylcellulose, hydroxypropylcellulose, hydroxypropylmethylcellulose, methylhydroxypropylcellulose, gelatin, polyethylene glycol fatty acid esters, polyvinylpyrrolidone, magnesium aluminium silicate and polyacrylamides.

Appreciable amounts, if not all, of the biologically active material in the solid or liquid formulations of this invention tend to survive passage through the hydrolytic and proteolytic environment of the stomach. For added protection, it is possible to formulate solid or liquid formulations in accordance with the invention in an enteric-coated or otherwise protected form. In the case of liquid formulations, they can either be mixed or simply coadminstered with a protectant, such as a liquid mixture of medium chain triglycerides, or they can be filled into enteric capsules (for example of soft or hard gelatin, which are themselves optionally additionally enteric coated), whereas solid formulations can be treated more flexibly: they can either be coated with enteric materials to form tablets or they can be filled into enteric capsules. The thickness of enteric coating on tablets or capsules can be, for example, from 0.5 to 4 microns in thickness, although the precise thickness will be determined by the skilled formulator. Enteric coated granules (whose particle size may be, for example, from 0.5 to 2 mm) may themselves be coated without being compounded into a tablet for coating. Microcapsules, similarly, can be enteric coated. The enteric coating may comprise any of the enteric materials conventionally utilised in orally administerable pharmaceutical formulations. Suitable enteric coating materials are known, for example, from "Remington's Pharmaceutical Sciences", 15th Edition, pp. 1614–1615 (1975); 2nd Edition, pp 116–117, 371–374 (1976); and "Hagers Handbuch der Pharmazeutischen Praxie", 4th Edition, Volume 7a (Springer Verlag 1971), pages 739 to 742 and 776 to 778.

Examples of suitable enteric coating materials include cellulose acetylphthalate, hydroxypropylmethylcellulosephthalate (HPMC-P), benzophenyl salicylate, cellulose acetosuccinate, copolymers of styrene and maleic acid, formulated gelatin, keratin, stearic acid, myristic acid, polyethylene glycol, shellac, gluten, acrylic and methacrylic resins and copolymers of maleic acid and phthalic acid derivatives. The enteric coating material(s) may be dissolved in solvents such as dichloromethane, ethanol and water, cellulose phthalate, or polyvinyl acetate phthalate. It is preferred to utilise HPMC-P, polyethylene glycol 6000 or shellac as the enteric coating. A proprietary preparation of HPMC-P aimed at dissolution or dissipation at pH 5.5, which is encountered in the human pyrolus, is available under the trade mark HP5-5, and is particularly preferred.

A particularly convenient way of administering formulations in accordance with the invention is to provide enteric-coated hard gelatin capsules. Although there is not necessarily any problem with coating hard gelatin capsules with certain enteric-coating materials, there is a difficulty with coating such capsules with the preferred HPMC-P coating material. The difficulty is that HPMC-P is usually coated in a pan-coater from a methylene chloride solution, and this solution tends to degrade the hard gelatin capsule.

According to a further aspect of the invention there is provided a process for preparing an enteric coated gelatin capsule, the process comprising first coating the capsule with material capable of protecting the gelatin of the capsule from detrimental effects of methylene chloride and subsequently coating the thus protected capsule with hydroxypropylmethylcellulose phthalate (HPMC-P) by means of a solution of HPMC-P in methylene chloride.

By means of a the protective "undercoat", the capsule is thus protected from the effects of the solvent for an optimum coating agent.

Suitable protective undercoats include PVP-F, HPMC, AVICEL (Crystalline cellulose) and HPC; HPC is not so preferred, as it does not have such good film-forming ability as other coating materials. Any other protective undercoat which can be coated in a fashion not detrimental to the gelatin capsule may also be used; suitable coating methods include deposition from a solution (eg 5% v/w) in a solvent (such as ethanol) which does not substantially adversely affect the gelatin under the conditions used. It may be possible to increase the range of suitable solvents by reducing the temperature of the coating operation (eg in a pan or rotating drum coater) from the conventional 80° C. to a lower level, such as 50° C. or below, 40° C. or below or preferably about 35° C., for ethanol.

Mixtures of "undercoat" materials can be used. A mixture of PVP and HPMC is particularly preferred. The weight ratio of PVP (eg PVP-F):HPMC may range from 0.1:1 to 20:1, preferably 0.2:1 to 5:1 and is optionally about 0.5:1 on a w/w basis. Coating may be carried out with from 1 to 10% (w/w, based on the total capsule weight) PVP-F and 2 to 20% (on the same basis) HPMC; amounts of 5% and 10%, respectively, are preferred.

The HPMCP can then be coated from a methylene chloride solution (eg about 5% w/v) as is conventional. This operation, like the undercoating, may take place in a pan coater or a rotating drum coater, preferably at a similarly reduced temperature. The HPMCP is preferably HP5-5, and it may be coated to an amount of 5–40%, preferably 15–25% and optionally about 20% w/w, based on the weight of the capsules.

Formulations in accordance with the invention can therefore be administered orally, but in a wide variety of different ways. An advantage of the orally administrable formulations of the invention is that enteric coatings are usually not necessary. Furthermore, high serum levels indicate that biologically active materials administered by means of the invention have high bioavailability. Furthermore, physiologically significant serum levels can be achieved very quickly by means of formulations in accordance with the invention.

For rectal administration, liquid or solid formulations can be administered as an enema or in suppository form. The suppository base may be cocoa butter or any other suitable material.

According to a further aspect of the invention, there is therefore provided a method of treating a human or other animal, comprising the oral or rectal administration of a formulation in accordance with the first aspect of the invention. In particular, the invention extends to the treatment of diabetes by the rectal or preferably oral administration of a formulation in accordance with the invention in which the biologically active material is insulin.

The invention also extends to the use of the ingredients of formulations in accordance with the first aspect of the invention in the preparation of an orally or rectally administrable formulation for the treatment or prophylaxis of disorders treatable or controllable by a biologically active material.

In particular, insulin can be used in the preparation of a formulation for the treatment or control of diabetes. Salmon calcitonin can be used in the treatment of high bone turnover (for example in Paget's disease of the bone), acute hypercalcaemia associated with malignancy and osteoporosis. Porcine somatotrophin can be administered to pigs to reduce the raising time of pigs and possibly to reduce the thickness of back fat.

The invention will now be illustrated by the following non-limiting examples. The examples refer to the accompanying drawings, in which:

A BRIEF DESCRIPTION OF THE DRAWINGS

EXAMPLE 1

Figure 1:
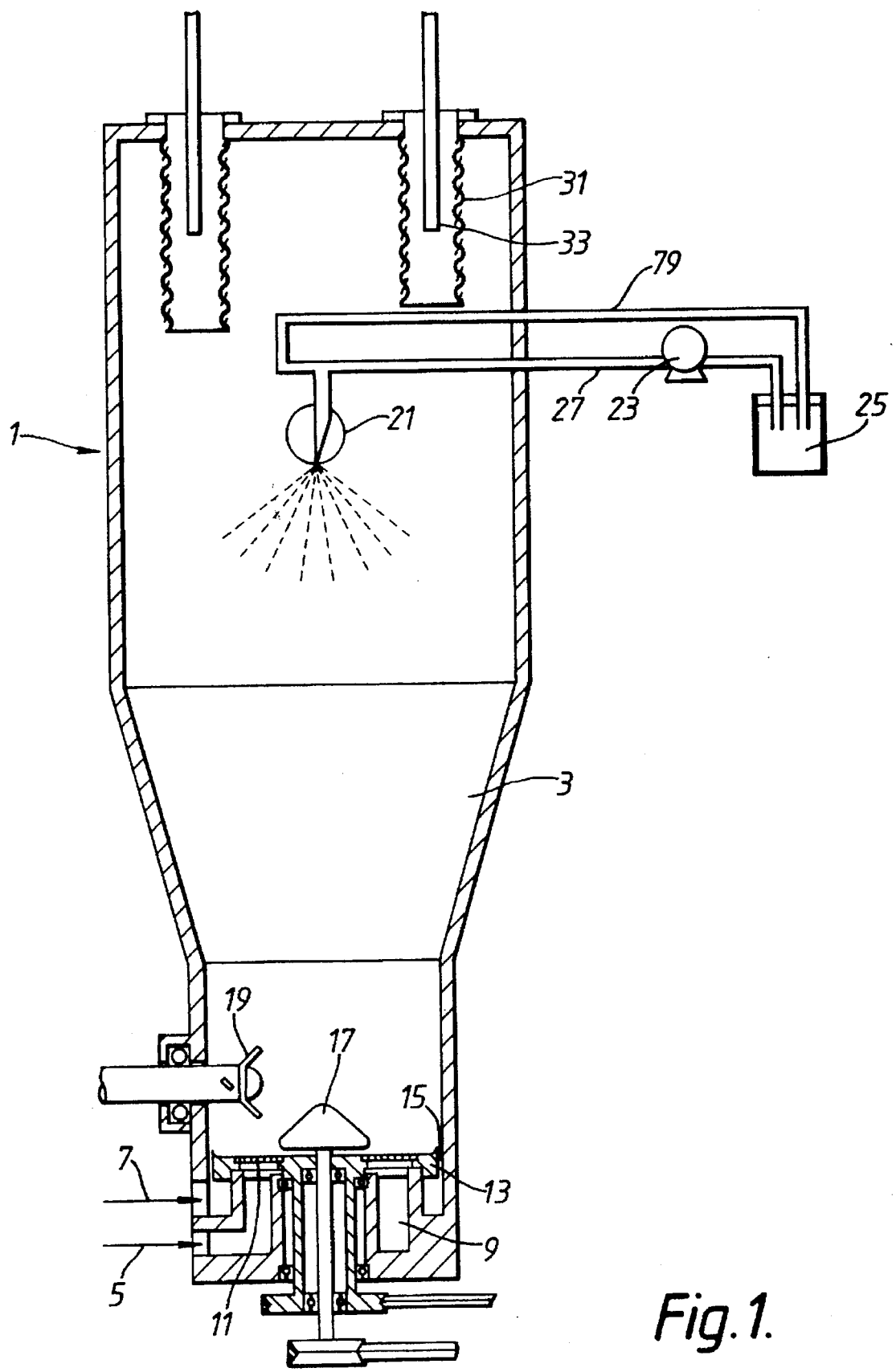
FIG. 1 shows a part-sectional/part-schematic view of a modified SPIR-A-FLOW apparatus as used in Example 8.

A liquid orally administrable insulin-containing formulation is prepared as follows. All chemicals used in this and the other examples are of analytical or chemical grade. First, Sub-Mixture A is prepared from the following ingredients:

| | |
|---|---|
| Egg yolk lecithin | 63.0 g |
| Glycerol mono-oleate (low HLB surfactant) | 22.46 g |
| Cholesterol | 30 g |
| Ethanol (95%) | 100 g | by heating the ethanol to 75° C., adding the glycerol monooleate, lecithin and cholesterol, stirring until all the chemicals are dissolved and cooling the mixture to room temperature (22° C).

An Anti-oxidant Sub-Mixture is prepared from the following ingredients:

| | |
|---|---|
| Propyl gallate | 37.5 g |
| Butylated hydroxyanisol (BHA) | 25.0 g |
| Butylated hydroxytoluene (BHT) | 37.5 g |
| Ethanol (95%) | to 100 ml | by dissolving the three anti-oxidant components in the ethanol at room temperature.

Sub-mixture B is prepared from the following ingredients:

| | |
|---|---|
| Oleic acid (emulsification aid) | 420 g |
| D-alpha-tocopherol (anti-oxidant) | 30 g |
| Polysorbate 80 (emulsification aid) | 30 g |
| Anti-oxidant Sub-mixture | 2.7 g |
| Ascorbic acid (anti-oxidant) | 1.2 g |
| Propylparaben (antimicrobial agent) | 1.2 g |
| Methylparaben (antimicrobial agent) | 6.8 g |
| Sub-Mixture A | 300 g |
| Ethanol (95%) | 750 g | by mixing them together at room temperature.

Sub-mixture C is prepared from the following ingredients:

| | |
|---|---|
| Insulin (Bovine, 24.6 IU/mg, CP Pharmaceuticals, UK) | 2.5 g |
| Citric acid (pH adjuster/enzyme inhibitor) | 2.6 g |
| Aprotinin proteinase inhibitor | 200,000 KIU × 15 |
| Ethanol (95%) | to 300 ml | by dissolving the solid ingredients in 100 ml of the ethanol and adding the remainder of the ethanol.

Sub-mixture D is prepared from the following ingredients:

| | |
|---|---|
| Polyoxyethylene (40) stearate (High HLB surfacatant) | 6 g |
| Hydroxypropyl cellulose (Stabiliser) | 30 g |
| Sodium benzoate (Antimicrobial agent) | 6 g |
| Deionised water | to 400 ml | by dissolving the first three ingredients in the water at room temperature.

Having prepared the various sub-mixtures, an insulin-containing water-in-oil microemulsion is prepared from the following amounts of the submixtures:

| | |
|---|---|
| Sub-mixture B | 450 ml |
| Sub-mixture C | 150 ml |
| Sub-mixture D | 150 ml | by adding Sub-mixture C slowly to Submixture D while stirring with an AUTOHOMOMIXER homogeniser at 7500 rpm at 20° C. The resultant mix is slowly added into Sub-mixture B using the same mixer at the same temperature and speed. The resulting emulsion is passed five consecutive times through a microfluidiser (model APV 15M8BA) under the following conditions:

Air flow: 2 dm$^3$/min.

Air pressure: 5000 psi (35 MN/m$^2$)

Cooling chamber temp.: 1.5° C.

The droplet size of the resulting microemulsion is on average about 1 micron.

EXAMPLE 2

A liquid orally administrable insulin-containing formulation is prepared by following the procedure of Example 1 with the following modifications:

1. Sub-mixture A contains 15 g of cholesterol instead of 30 g;
2. Sub-mixture B contains 200 g of Sub-mixture A, instead of 300 g and additionally contained 150 g of PVP-chylomicron preparation.
3. Submixture D contains 6 g polyethylene glycol monostearate as the high HLB surfactant instead of the polyoxyethylene (40) stearate.

EXAMPLE 3

A solid orally administrable insulin-containing formulation is prepared as follows. Solid core carrier particles are prepared by mixing the following components:

| | |
|---|---|
| Ca carboxymethyl cellulose | 200 g |
| Alginic acid | 75 g |
| Gelatin | 50 g |
| Hydroxypropyl cellulose | 175 g |
| Sodium lauryl sulphate | 25 g | at 22° C. A test sample shows that the particles swell to 200 times their original volume when immersed in water at 38° C.

The core particles are dried in a GLATT (trade mark) fluidised bed at 29° C. for 45 minutes. Subsequently, 800 g of the particles are coated with 1000 ml of the liquid formulation of Example 1 in a SPHERONIZER Model 15 fluid bed coater/dryer. (The word SPHERONIZER is a trade mark of G. B. Caleva Ltd, Ascot, Berkshire.)

EXAMPLE 4

An enteric coated particulate solid orally administrable insulin-containing formulation is prepared by taking the coated particles prepared in Example 3 and further coating them with the following solution:

| | |
|---|---|
| HPMC-phthalate | 65 g |
| Ethanol (95%) | 650 ml |
| Methylene chloride | 650 ml | in a centrifugal turn-table spray-coater.

EXAMPLE 5

Capsules of a particulate solid orally administrable insulin-containing formulation are prepared by packing an appropriate amount of the particulate solid prepared in Example 3 into hard gelatin capsules sizes 0–4.

EXAMPLE 6

Capsules of an enteric coated particulate solid orally administrable insulin-containing formulation are prepared by packing an appropriate amount of the enteric coated particulate solid prepared in Example 4 into hard gelatin capsules sizes 0–4.

EXAMPLE 7

The process of Example 1 is repeated, except that in sub-mixture B 16 g (20 ml) of refined (pharmaceutical grade) sesame oil is added and the amount of oleic acid is reduced by 16 g to 404 g. The sesame oil provides enhanced antioxidant activity and improves the flavour of the compositions (especially to oriental patients), thereby improving patient compliance.

EXAMPLE 8

A solid orally administrable insulin-containing formulation is prepared as follows. Solid core carrier particles are prepared as in Example 3. 800 g of the particles are coated with 1000 ml of the liquid formulation of Example 7 in a modified SPIR-A-FLOW fluid bed coater/drier as follows: (SPIR-A-FLOW is a trade mark of Freund International Ltd, Tokyo, Japan.)

The fluid bed coater/drier is shown, part-sectionally and part schematically in FIG. 1, where it is represented generally by reference numeral 1.

The coater/drier 1 comprises a chamber 3 supplied with fluid air through inlet 5 and slit air through inlet 7. The fluid air from inlet 5 enters into a fluid air inlet chamber 9, from which it passes, through a cross-meshed annular gauze 11 into the chamber 3. The annular gauze 11 is set in a rotor 13, which defines a generally flat bottom of the chamber 3. The rotor 13 defines an annular slit 15 with the periphery of the lower part of the chamber 3, and slit air from the inlet 7 enters into the chamber 3 through the slit 15. Although conventional coater/driers have an agitator, which rotates coaxially with the rotor 13, such an agitator is not present in the coater/drier 1. Instead, a generally conical boss 17 is located where an agitator would normally be seated, and serves to protect the bearings of the rotor 13 from excessive penetration by particles from the chamber.

Radially located in the wall of the chamber is a rotating lump breaker 19, generally in the shape of a plurality of rotating blades.

In the upper part of the chamber 3 there is a nozzle 21 for downwardly spraying liquid formulation into the chamber. The nozzle 21 is fed by a pump 23 from a reservoir 25 of liquid formulation. Supply is by means of a feed pipe 27 and a return pipe 29 for excess liquid. An air supply to (and return from) the nozzle causes an appropriate spray.

Located at the uppermost part of the chamber 3 are a pair of back filters 31 through which fluidizing air is filtered before leaving the chamber 3. Located in each bag filter 31 is a pulse jet 33 for supplying pulses of air to dislodge particles on each bag filter 31.

In use of the apparatus, solid core carrier particles are introduced into the chamber 3 by means of a door (not shown). The door is then closed, and the fluidizing air supply to the coater/drier is turned on. The air supply is at a pressure of 100 mm of water and is dehumidified and filtered to remove microbes and any particles of oil that may have been transported from the compressor apparatus (not shown). The supply air temperature is normally 40° C. Fluidizing air enters through inlet 5 and the rotating annular mesh 11 at a rate of 4 liters per minute and at a pressure of 50 mm of water to fluidize the carrier particles in the chamber. Slit air enters through the annular slit 15 also at a rate of 4 liters per minute but at a lower pressure of 5 to 10 ml of water to help keep the particles away from the all of the chamber 3. The lump breaker 19 is set to rotate at 2,500 rpm, and the rotor 13 is set to rotate at 250 rpm. The boss 17, which takes the place of a rotating agitator coaxial with the rotor 13 does not significantly rotate, but may gently revolve to keep the bearings free.

The liquid formulation of Example 7 is placed in the reservoir 25 and is pumped by means of the pump 23 through the supply line 27 to the nozzle 21, where it is sprayed into the fluidized carrier particles. Liquid formulation is pumped through the supply line 27 at the rate of 12.2 mls per minute, and air is supplied to the nozzle, in supply and return lines (not shown) for the purpose of causing an appropriate spray. The spray air is supplied at 2.3 liters per minute at a pressure of 1.2 kgf/cm$^2$.

Liquid formulation is sprayed for 10 seconds, and then switched off from 15 seconds, but the fluid air and slit air are continuously supplied to keep the carrier particles fluidized.

If the temperature inside the chamber 3 begins to rise above 30° C., the temperature of the supply air is lowered from 40° C. In order to effect a rapid cooling if necessary, means (not shown) are supplied to cool the supply air, to ensure that the temperature of the sprayed particles does not substantially exceed 30° C.

The process is continued until 1000 ml of the liquid formulation of Example 7 has been coated on the 800 g of the carrier particles.

EXAMPLE 9

Capsules of a particulate solid orally-administrable insulin formulation are prepared by packing an appropriate amount of the particulate solid prepared in Example 8 into hard gelatin capsules, sizes 0–4.

EXAMPLE 10

To prepare 1 liter of an orally ingestible salmon calcitonin formulation, the following procedure is followed. First the following ingredients are used to prepare the hydrophilic phase:

| | |
|---|---|
| Polyoxyethylene 40 stearate | 6.7 g |
| Sodium benzoate | 12.0 g |
| Hydroxypropyl cellulose SL | 6.0 g |
| Aprotinin (TRASYLOL sol$^n$) | 200,000 KIU × 15 |
| Citric acid | 4.3 g |
| Ascorbic acid | 3.2 g |
| Deionised water | 166.7 ml |

The procedure used is to dissolve the hydroxypropyl cellulose in the TRASYLOL (trade mark) aprotinin solution and to mix this with the POE(40) stearate, the sodium benzoate and the citric acid ascorbic acids. The water is added, and the mixture is mixed in an AUTOHOMOMIXER to dissolve the components. The pH is adjusted to between 3.0 and 3.25 by slowly adding a concentrated solution of citric and ascorbic acids.

To the resulting hydrophilic aqueous phase, salmon calcitonin (supplied by Rorer; also available from Sigma Chemical Co, St. Louis, Mo., USA) is slowly added with constant mixing at room temperature and with a relative humidity of less than 40%. Sufficient salmon calcitonin is added to make 600 to 1200 IU per ml of the final formulation; 1000 IU per ml is the chosen amount.

Separately, the hydrophobic phase is prepared from the following ingredients:

| | |
|---|---|
| Egg yolk lecithin | 32.8 g |
| Cholesterol | 26.7 g |
| d-alpha-tocopherol | 1.3 g |
| Glycerol monooleate | 23.7 g |
| Oleic acid | 212.0 g |
| Tween 80 | 157 g |
| Antioxidant submixture | 2.8 g |
| Propyl paraben | 3.0 g |
| Methyl paraben | 20.0 g |
| Sesame oil (pharm. grade) | 6.7 g |
| Ethanol (95%) | q.s. |

The process used is to mix together the cholesterol, tocopherol, glyceryl monooleate and other ingredients in the ethanol, whose volume is chosen so that the volume of the hydrophobic phase is the same as that of the hydrophilic phase. (The antioxidant solution is prepared as in Example 1, but optionally omitting the BHA and BHT.) The resulting solution is mixed together thoroughly. An AUTOHOMOMIXER homogeniser operating at 7500 rpm at 20° C. may be used, but simple mechanical or magnetic mixing may be sufficient. The hydrophilic phase is then poured into an equal volume of the hydrophobic phase while stirring. Again, simple mechanical agitation may be sufficient or an AUTOHOMOMIXER homogeniser operating under the same conditions as above may be used. The resulting emulsion is passed three consecutive times through the same microfluidiser used in Example 1 using the same conditions.

EXAMPLE 11

A solid orally administrable salmon calcitonin containing formulation was prepared broadly as described in Example 8, except that 500 ml of the liquid formulation of Example 10 was coated onto 400 g of carboxymethylcellulose, calcium salt in the modified SPIR-A-FLOW apparatus.

EXAMPLE 12

Capsules of a particulate solid orally administrable salmon calcitonin formulation are prepared by packing an appropriate amount of the particulate solid prepared in Example 11 into hard gelatin capsules, sizes 0–4.

EXAMPLE 13

Enteric coated hard gelatin capsules of an orally administrable salmon calcitonin formulation are prepared as follows. The capsules of Example 12 are coated in a HI-COATER rotating drum coater with 5% PVP-F and 10% HPMC in ethanol. The percentages are based on the weight of the capsules. (The word HI-COATER is a trade mark of Freund International Ltd, Tokyo, Japan.) The capsules, which have thus been coated with an undercoat, are then coated with 20% (by weight, base don the capsule weight) of HP5-5 (which is a composition of HPMCP aimed at pH 5.5) in methylene chloride, again in the HI-COATER rotating drum coater. The capsules are then ready for oral administration.

EXAMPLE 14

An orally ingestible porcine somatotrophin (PST) formulation is prepared as follows.

Sub-mixture A is prepared from the following ingredients:

| Soya lecithin | 150 g |
| --- | --- |
| Glyceryl monooleate | 22.46 g |
| Cholesterol | 30 g |
| Ethanol | 50 ml | by dissolving the first three ingredients in warm (75° C.) ethanol and stirring until the other ingredients are dissolved. The ethanol is then evaporated off.

Sub-mixture B is prepared from the following ingredients:

| Oleic Acid | 420 g |
| --- | --- |
| d-alpha-tocopherol | 30 g |
| Polysorbate 80 | 30 g |
| Anti-oxidant sub-mixture (from Example 1) | 2.7 g |
| Propylparaben | 1.2 g |
| Methylparaben | 6.8 g |
| Sub-mixture A | 300 g |
| Ethanol (95%) | 750 g | by mixing them together at room temperature.

Sub-mixture C is prepared from the following ingredients:

| Porcine somatotrophin (from American Cyanamid; also available from Sigma) | 50 mg |
| --- | --- |

-continued

| Aprotinin | 200,000 KIU |
| --- | --- |
| Sodium carbonate sol$^n$ | 300 cm$^3$ | by mixing at room temperature. The pH is adjusted to 5.0 with phosphate buffer.

Sub-mixture D is prepared as in Example 1, except that the polyoxyethylene (40) stearate is omitted.

Having prepared the various sub-mixtures, a porcine somatotrophin-containing microemulsion is prepared from the following amounts of the sub-mixtures:

| Sub-mixture B | 450 ml |
| --- | --- |
| Sub-mixture C | 150 ml |
| Sub-mixture D | 150 ml | by adding sub-mixture C slowly to sub-mixture D while stirring with an AUTOHOMOMIXER homogeniser at 7500 rpm at 20° C. The resultant mix is slowly added into sub-mixture B using the same mixer at the same temperature and speed. The resulting emulsion is passed five consecutive times through a microfluidiser, as in Example 1, under the same conditions.

EXAMPLE 15

A solid orally administrable PST-containing formulation is prepared as follows. Solid core carrier particles are prepared by mixing the following components:

| Soya bean powder | 300 g |
| --- | --- |
| Hydroxypropyl cellulose | 50 g |
| Alginic acid | 50 g | at 22° C. The core particles are dried in a GLATT (trade mark) fluidising bed at 29° C. for 45 minutes. Subsequently, 500 ml of the liquid formulation prepared in Example 14 is sprayed onto the dried core particles in the modified SPIR-A-FLOW apparatus described in Example 8.

EXAMPLE 16

The coated particles resulting from Example 15 are granulated in a CF Granulator (Freund Industries, Inc, Tokyo, Japan) to a particle size of 1.5–2 mm. Broadly, conventional conditions and/or those recommended by the manufacturer are used. A solution (approximately 8% w/v) of hydroxypropylcellulose-L (HPC-L) in ethanol is used to agglutinate the particles to granules. The granules are then enteric coated with 8% (by weight based on the weight of the granules) HPMC-P, supplied from a 5% (w/v) solution in methylene chloride in a pan or drum coater. Finally, the coater is used to provide a wax coat on the enteric granules in an amount sufficient to enable the granules to float in the pig's stomach when ingested by a pig.

EXAMPLE 17

Using the general procedure of Example 7, but substituting an appropriate amount of human insulin, rather than bovine insulin, a corresponding orally ingestible human insulin formulation is prepared. The liquid formulation may be coated on a solid carrier as described in Example 8.

EXAMPLE 18

Using the general procedure of Example 7, but substituting an appropriate amount of human interferon-gamma, rather than bovine insulin, a corresponding orally ingestible human interferon-gamma formulation is prepared. The liquid formulation may be coated on a solid carrier as described in Example 8.

EXAMPLE 19

Using the general procedure of Example 7, but substituting an appropriate amount of human interferon-beta, rather than bovine insulin, a corresponding orally ingestible human interferon-beta formulation is prepared. The liquid formulation may be coated on a solid carrier as described in Example 8.

EXAMPLE 20

Using the general procedure of Example 10, but substituting an appropriate amount of erythropoietin, rather than bovine insulin, a corresponding orally ingestible erythropoietin formulation is prepared. The liquid formulation may be coated on a solid carrier as described in Example 8.

EXAMPLE 21

Using the general procedure of Example 14, but substituting an appropriate amount of tissue plasminogen activator, rather than bovine insulin, a corresponding orally ingestible tissue plasminogen activator formulation is prepared. The liquid formulation may be coated on a solid carrier as described in Example 8.

EXAMPLE 22

Using the general procedure of Example 14, but substituting an appropriate amount of Factor VIII, rather than bovine insulin, a corresponding orally ingestible Factor VIII formulation is prepared. The liquid formulation may be coated on a solid carrier as described in Example 8.

BIOLOGICAL EXAMPLE A

Clinical Test of Orally Administrable Preparation of Example 5

A total of 17 diabetics (8 Insulin-Dependent and 9 Non-Insulin-Dependent diabetics) and one healthy male volunteer are fasted overnight. All oral hypoglycemic agents and insulin injections are withheld from these patients for at least 12 hours before the study. Each diabetic is given per os the orally administrable formulations of insulin prepared in Example 5 (hard gelatin capsule containing the core carrier particles spray-coated with insulin-bound microemulsion but not enteric coated). Each capsule contains approximately 10 U of bovine insulin and each subject is given, orally, a dose equivalent to approximately one unit per kg body weight, with about 250 ml of water. Blood sugar levels are measured on blood samples obtained by pricking the fingertip using a HAEMOGLUKOTEST set 20-800R and a REFLOLUX apparatus (Boehringer Mannheim GmbH, West Germany). In a few cases, serum insulin levels are measured using a radioimmunoassay method. For the serum insulin analyses, the serum samples are decanted into TRASYLOL-containing test tubes and stored at −20° to −35° C. until analysed. (TRASYLOL is a trade mark of Bayer for aprotinin proteinase inhibitor.)

Blood sugar levels are shown in Table 1 below.

TABLE 1

Demography of Diabetics and One Healthy Volunteer Orally Ingesting the Example 5 Capsules

| Case | Sex | Age | Class of Diabetes | Blood Sugar (mg/dl) | | | | | |
|---|---|---|---|---|---|---|---|---|---|
| | | | | 0 | 1 | 2 | 3 | 4 | (Hours) 5 |
| 1 | m | 58 | IDDM | 254 | 127* | | | | |
| 2 | m | 67 | NIDDM | 216 | 196 | 186+ | | | |
| 3 | f | 51 | IDDM | 180 | 142 | | | | |
| 4 | m | 50 | IDDM | 152 | 115 | 98 | | | |
| 5 | m | 68 | IDDM | 301 | 283 | 213+ | | | |
| 6 | m | 45 | NIDDM | 190 | | 167+ | | | |
| 7 | m | 60 | IDDM | 173 | 148 | | | | |
| 8 | m | 53 | NIDDM | 205 | | 101 | | | |
| 9 | f | 45 | NIDDM | 193 | 147 | | 112 | | |
| 10 | m | 54 | NIDDM | 164 | 147 | 143 | | | 135+ |
| 11 | f | 48 | IDDM | 209 | 203 | 173 | | | |
| 12 | f | 54 | NIDDM | 154 | 115 | 96 | | | |
| 13 | m | 35 | NIDDM | 167 | 162 | 148 | | | |
| 14 | m | 70 | NIDDM | 256 | | 162+ | | | |
| 15 | m | 57 | NIDDM | 253 | | 229 | 177 | | |
| 16 | m | 31 | Healthy | 116 | | 128 | 149 | 127 | 117 |
| 17 | m | 40 | IDDM | 252 | 162 | | 133 | | |
| 18 | m | 40 | IDDM | 157 132 | 118 | 61 | 60* | 75 | 99 |

*Insulin-Induced Shock
+Resistant to s.c. injected Regular Insulin (5 to 20 units)

Some patients respond poorly to subcutaneously injected insulin (specifically, Case Nos. 2, 5, 6, 10 and 14). They exhibit the following blood sugar response to Regular Injected insulin:

TABLE 2

| Case | Sex | Age | Class of Diabetes | Units of Regular Insulin, s.c. | Blood Sugar (mg/dl) | | | |
|------|-----|-----|-------------------|-------------------------------|-----|-----|-----|-----------|
|      |     |     |                   |                               | 0   | 1   | 2   | 3 (hours) |
| 5    | m   | 68  | IDDM              | 15                            | 171 | 196 | 161 | 170       |
| 6    | m   | 45  | NIDDM             | 5                             | 259 |     | 376 | 298       |
| 2    | m   | 67  | NIDDM             | 20                            | 216 | 196 | 186 | 180       |
| 10   | m   | 54  | NIDDM             | 20                            | 330 |     | 180 |           |
| 14   | m   | 70  | NIDDM             | 20                            | 312 | 162 |     |           |

The orally administrable preparation of Example 5 (without enteric coating on the particles) is thus effective in lowering the elevated fasting blood sugar levels to or at least toward normal blood sugar levels in all diabetics studied, except in one case (Case No. 11) where the observed decrease in blood sugar levels is not considered to be clinically significant. The healthy volunteer does not respond to the orally administered formulation of Example 5. Two cases (Case Nos. 1 and 18) develop an insulin-induced hypoglycaemic shock at some 75 and 120 minutes, respectively, after oral administration of the formulation of Example 5, which is managed by ingestion of 100 gm of sugar water.

In a few cases studied, a series of serum samples are collected before and following the oral intake of the formulation of Example 5. The results are as follows in Table 3:

An appropriate amount of the microemulsion is given in a liquid form per os together with 10 ml of MCT (MCT is a trade mark for a medium chained triglyceride solution by Mead-Johnson & Co. Evansville, Ind., U.S.A.). The MCT microemulsion preparation behaves as if the insulin-containing microemulsion had been enteric coated. Each ml of the insulin-containing formulation contains approximately 5 units of bovine insulin.

Twelve diabetics (9 IDDM and 3 NIDDM) and one healthy male volunteer participate in the study. All patients are fasted overnight, and oral hypoglycaemic agents and insulin are withheld for 12 or more hours. Each subject is given one unit of insulin per kg body weight in the form described above per os. The results are as follows:

TABLE 3

Serum Insulin (mcU/ml) and blood sugar (mg/dl) levels after orally ingesting Example 5 capsules

| Case | Sex | Age | Class of Diabetes | Sample | Serum Insulin (micro-U/ml) and Blood Sugar mg/dl) Levels | | | | | | | |
|------|-----|-----|-------------------|--------|-----|-----|-----|-----|-----|-----|-----|---------|
|      |     |     |                   |        | 0   | 0.5 | 1.0 | 1.5 | 2.0 | 3.0 | 4.0 | 5.0 hours |
| 10   | M   | 54  | NIDDM             | Insulin | 20 |     | 198 |     | 106 |     | 76  |         |
|      |     |     |                   | Blood Sugar | (166) | | (151) | | (145) | | (134) | |
| +After regular Insulin, 20 Units, s.c. injection | | | | Insulin | 24 | | 19 | | 11 | 15 | 14 | |
|      |     |     |                   | Blood Sugar | (157) | (102) | | (77) | | (106) | | |
| 18   | M   | 40  | IDDM              | Insulin | 6 | 160 | 140 | 106 | 58 | 50 | | 46 |
|      |     |     |                   | Blood Sugar | (157) | (132) | (118) | (61) | (60) | (75) | | (89) |
| +After Regular Insulin, 15 Units s.c. injection | | | | Insulin | 10 | | 57 | | | 184 | 98 | 64 |
|      |     |     |                   | Blood Sugar | (171) | | (152) | (131) | (122) | (207) | | |

Remarks: +Regular Insulin (Green Cross Co. of Seoul, Korea) isosubcutaneously (s.c.) injected to the study cases on separate date.
*Case No. 18 goes into an insulin-induced hypoglycemic shock at about 1.5 hours after the oral ingestion of the Example 5 Capsules, managed by oral administration of 100 Gas sugar in water.

BIOLOGICAL EXAMPLE B

Clinical Test of Orally Administrable Preparation of Example 1.

TABLE 4

| Case | Sex | Age | Class of Diabetes | Blood Sugar (mg/dl) 0 | 1 | 2 | 3 | 4 (Hours) |
|---|---|---|---|---|---|---|---|---|
| 1 | f | 46 | NIDDM | 190 | 174 | 167 | | |
| 2 | m | 68 | IDDM | 321 | | 144 | | |
| 3 | f | 52 | NIDDM | 161 | 139 | | | |
| 4 | m | 37 | IDDM | 207 | | 147 | | |
| 5 | m | 59 | IDDM | 307 | 285 | 173 | 109 | |
| 6 | m | 30 | IDDM | 244 | 212 | 202 | 170 | |
| 7 | f | 50 | IDDM | 153 | 136 | | | |
| 8 | m | 54 | NIDDM | 224 | 205 | 190 | | |
| 9 | m | 60 | IDDM | 153 | 78 | | | |
| 10 | m | 40 | IDDM | 157 | 125 | 110 *Insulin-shock | | |
| 11 | m | 58 | IDDM | 259 | 172 | 98 | | |
| 12 | m | 35 | IDDM | 156 | 137 | | | |
| 13 | m | 31 | Normal** | 157 | 112 | 107* | 92 | 83* Insulin-shock |

*Insulin-induced hypoglycemic shock
**This healthy male has an early breakfast, some two and one-half hours prior to the study; he experiences moderate to moderately severe insulin-induced hypoglycemic shock reaction with symptoms such as cold sweat, lack of physical coordination and hunger pains.

Case numbers 1 and 8 are poor responders both to 500 mg tablets, per os, of Diabensase and subcutaneously injected 20 units of Regular Insulin, as can be seen as follows:

In a few cases studied, a series of serum samples are collected before and following the oral intake of the formulation of Example 5. The results are as follows in Table 6:

TABLE 5

| Case | Sex | Age | Class of Diabetes | Regular Insulin/ Diabenase | Blood Sugar (mg/dl) 0 | 1 | 2 | 3 | 4 (Hrs) |
|---|---|---|---|---|---|---|---|---|---|
| 1 | f | 46 | NIDDM | 15 Units | 201 | 198 | | | 185 |
| | | | | 500 mgs | 186 | | | 164 | |
| 6 | m | 30 | IDDM | 20 Units | 151 | | 124 | | |
| 8 | m | 54 | NIDDM | 20 Units | 218 | | 200 | 194 | 176 |
| | | | | 500 mgs | | 222 | 205 | 174 | |

Only one diabetic out of 12 patients studied is a poor responder to the oral administration of insulin-containing

TABLE 6

Serum insulin (mcU/ml) and blood sugar (mg/dl) levels after orally ingesting the Example 1 emulsion

| Case | Sex | Age | Class of Diabetes | Sample | Serum Insulin (micro-Units/ml) and (Blood Sugar: mg/dl) Levels 0 | 0.5 | 1 | 1.5 | 2 | 3 | 4 | 5.0 (Hours) |
|---|---|---|---|---|---|---|---|---|---|---|---|---|
| 5 | m | 59 | IDDM | Insulin | 10 | | 158 | | | 188 | 107 | 84 |
| | | | | Blood Sugar | (307) | | (285) | | | (173) | (109) | (—) |
| 11 | m | 58 | IDDM | Insulin | 18 | 204 | 168 | | | 80 | | |
| | | | | Blood Sugar | (259) | (—) | (172) | | | (98) | | |
| +After Regular Insulin | | | | Insulin | 38 | 159 | | | | 78 | 45 | |
| 20 Units, s.c. injection | | | | Blood Sugar | (308) | (181) | | | | (87) | (115) | |
| 12 | m | 35 | IDDM | Insulin | | 15 | | 68 | | | 70 | 50 |
| | | | | Blood Sugar | | (156) | | (137) | | | (62) | (60) |
| +After Regular Insulin | | | | Insulin | 30 | | 47 | | | 112 | 115 | |
| 15 Units, s.c. injection | | | | Blood Sugar | (188) | | (181) | | | (160) | (139) | |

Remarks: +Regular Insulin (Green Cross Co. of Seoul, Korea) was subcutaneously (s.c.) injected to the study cases on a separate date.

microemulsion. The one healthy volunteer studied responds well and goes into an insulin-induced hypoglycaemic shock.

BIOLOGICAL EXAMPLE C

The same mixture as is orally ingested in Example 8 is administered as follows.

In two beagle dogs, weighing 12 and 16 kg respectively, 5 ml of Insulin-containing microemulsion (each ml containing 5 units of bovine insulin) are infused/injected over 5 minutes into the duodenum. The post-administration serum glucose and serum insulin (IRI) levels in the two dogs are as follows:

TABLE 7

Canine Serum Levels of Glucose and Insulin before and after an Intra-duodenal Administration of Insulin-Containing Microemulsion.

| Animal | | Serum Glucose Level (mg/dl)/ Serum Insulin Level (micro-unit/ml) | | | | | | | |
|---|---|---|---|---|---|---|---|---|---|
| No. | Sample | −0.5 | 0 | 0.5 | 1 | 1.5 | 2 | 3 | 4 | 5(Hrs) |
| A | Serum Glucose | 109.5 | 120.3 | 67.4 | 49.6 | 39.0 | 28.5 | 24.7 | 43.4 | 79.7 |
|   | Serum Insulin | 8 | 10 | 250 | 139 | 172 | 96 | 54 | 4 | 13 |
| B | Serum Glucose | 133.8 | 138.4 | 105.7 | 76.8 | 77.6 | 83.5 | 78.8 | 94.3 | 104.5 |
|   | Serum Insulin | 16 | 20 | 122 | 89 | 50 | 39 | 9 | 8 | 20 |

The intra-duodenal administration of Insulin-containing microemulsion induces a lowering in the blood sugar levels and a corresponding increase in the serum insulin levels in both dogs studied which is indicative of good bioavailability of orally/intra-duodenally administered insulin. So the insulin is both bioactive and bioavailable.

BIOLOGICAL EXAMPLE D

After fasting overnight, six male volunteers aged between 21 and 26 (mean 23.1) years old and whose weight is between 58 to 78 (mean 66) kg and whose height ranges between 171 to 187 (mean 177.2) cm participate in this study. At 6.00 am, five subjects orally ingest 400 to 420 IU of salmon calcitonin in the formulation of Example 10 and another one subject was subcutaneously injected with 200 IU of salmon calcitonin (CALCYNAR—registered trade mark) under fasting conditions. Systemic venous blood samples are collected at Time-0 (before the medication) and at 30, 60, 90, 120, 150, 180, 210, 240, 300, 360 and 480 minutes after the medication. Serum phosphate level from the collected blood samples is measured by the Fiske-Subarrow method, and the EDTA-treated plasma salmon calcitonin level is assayed by a radioimmunoassay method, using $^{125}I$ and rabbit salmon calcitonin antibody sera. All measurement are run in triplicate. The results are shown in Table 8.

TABLE 8

| | Plasma Salmon Calcitonin Level (pg/ml) | | | | | |
|---|---|---|---|---|---|---|
| Time (Min) | A Oral | B Oral | C Injection | D Oral | E Oral | F Oral |
| 0 | 10 | 10 | 10 | 10 | 10 | 10 |
| 30 | 10 | 10 | 260 | 102 | 10 | 10 |
| 60 | 10 | 15 | 170 | 15 | 21 | 10 |
| 90 | 10 | 10 | 102 | 10 | 10 | 190 |
| 120 | 130 | 10 | 10 | 170 | 10 | 10 |
| 150 | 10 | 86 | 10 | 11 | 10 | 10 |
| 180 | 460 | 66 | 68 | 92 | 68 | 10 |
| 210 | 10 | 180 | 10 | 66 | 10 | 66 |
| 240 | 10 | 10 | 10 | 81 | 10 | 21 |
| 300 | 10 | 10 | 66 | 10 | 10 | 10 |

TABLE 8-continued

| | Plasma Salmon Calcitonin Level (pg/ml) | | | | | |
|---|---|---|---|---|---|---|
| Time (Min) | A Oral | B Oral | C Injection | D Oral | E Oral | F Oral |
| 360 | 10 | 10 | 10 | 10 | 10 | 10 |
| 480 | 10 | 10 | 10 | 10 | 10 | 10 |

It can be seen that oral administration of salmon calcitonin at 400 to 420 IU as the formulation of Example 7 causes a broadly similar degree of reduction in serum phosphate levels and a similar rise in plasma RIA-measured salmon calcitonin to that provided by a 200 IU subcutaneous injection in men.

The oral delivery form of salmon calcitonin as prepared in Example 10 causes peaking of salmon calcitonin in human plasma and reduction in serum phosphate levels in young male volunteers. The oral salmon calcitonin at 400 to 420 IU induces a broadly similar biological response (measured as reduction in serum phosphate) and salmon calcitonin bioavailability in EDTA-treated plasma (assayed by RIA) in men to 200 IU salmon calcitonin injected subcutaneously. Salmon calcitonin incorporated in the Example 7 formulation is biologically effective and bioavailable in man after oral ingestion.

BIOLOGICAL EXAMPLE E

To a male pig weighing 75 kg, 500 micrograms of oral porcine somatotrophin (PST) (as prepared in Example 16) per kg body weight is placed in the stomach via gastric tube, and to another male pig weighing 82 kg, 500 micrograms of oral PST per kg of body weight is administered into the duodenum via enterostomy.

Blood samples are collected via a chronic intravenous cannula placed into a jugular vein and serum PST is measured from each sample by radioimmunoassay.

In these two pigs, which had been pre-tested with daily intramuscular injections of 500 mg dexamethasone for three consecutive days (to suppress in vivo secretion of PST), both intra-gastric and intra-duodenal administration of PST, 500 micrograms per kg body weight, show bioavailability of PST peaking at 6 hours post intra-duodenal and 10 hours after intra-gastric administration. The results are shown in Table 9.

TABLE 9

Porcine Somatotrophin levels in pigs.

| Time After Administration (Hours) | Serum PST (ng/ml) | |
|---|---|---|
| | Pig (Gastric) | Pig 2 (Duodenal) |
| 0 | 5 | 5 |
| 2 | 7 | 5 |
| 4 | 6.5 | 12 |
| 6 | 6.5 | 17 |
| 8 | 13 | 17 |
| 10 | 14 | 15 |
| 12 | 14 | 13 |
| 14 | — | 13.5 |
| 16 | — | 13.5 |
| 24 | 9 | — |

The PST, administered into the stomach or duodenum, therefore appears to be bioavailable.

BIOLOGICAL EXAMPLE F

This example demonstrates that insulin in a formulation of the invention is absorbed through the lymphatic vessel(s) and not via the 'pore system' of the membrane (in which case, no insulin should be found in lymph fluid, and most of the absorbed insulin would be found in the portal vein draining into the liver).

A female pig, weight 35 kg is anesthetized and the duodenum was exposed. A cannula is inserted into the duodenum; the major lymph vessel draining from the duodenum is cannulated and lymph fluid is collected into a cylinder over every 15 minute period throughout the entire period of the study. Another cannula is inserted into the portal vein and its opening tip is advanced into the liver; a catheter is placed into the right jugular vein; and a cannula is placed into the left forearm vein and 10% glucose in water is infused, intravenously.

A liquid insulin-containing formulation (50 ml—each ml containing 5 U of bovine insulin), prepared as in Example 1 is infused rapidly into the duodenum through the cannula placed into the lumen of the duodenum at Time-0.

Serum and lymph fluid insulin are assayed by radioimmunoassay. The lymph fluid is diluted one to ten because of high insulin levels found in the samples, and it is found to need further dilution to 1/50 for the lymph sample collected at 15–30 minutes of the study.

Figure 2:
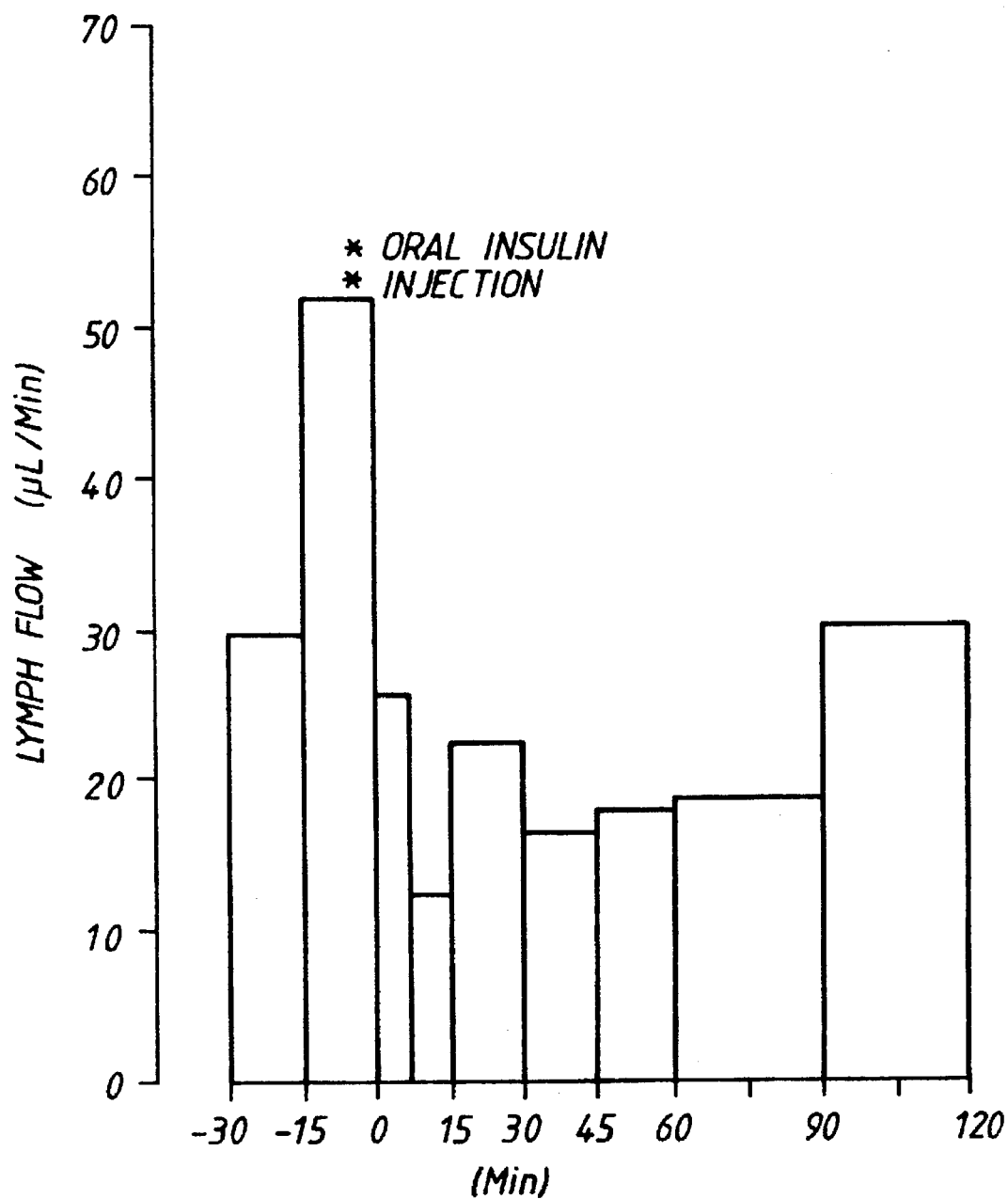
FIG. 2 is a bar chart of lymph flow against time in Biological Example F.

The major lymph vessel draining duodenum, after its cannulation and under anesthesia shows a slight tendency in reduction in its flow rate. The exception is a transitory elevation in the flow rate observed prior to intra-duodenal administration of ODDS-Insulin, which may be due to anesthetic applied in this study. The lymph flow is shown in FIG. 2.

After intra-duodenal infusion of the insulin formulation, a transitory elevation of serum insulin level is found from the hepatic portal blood sampled at 7.5–15 minutes after the medication. Otherwise, serum insulin levels are not altered in the hepatic portal blood samples throughout the study, as is shown graphically in FIG. 3B. No changes in the serum insulin levels are found from the systemic venous blood samples, as is shown graphically in FIG. 3A.

Figure 3C:
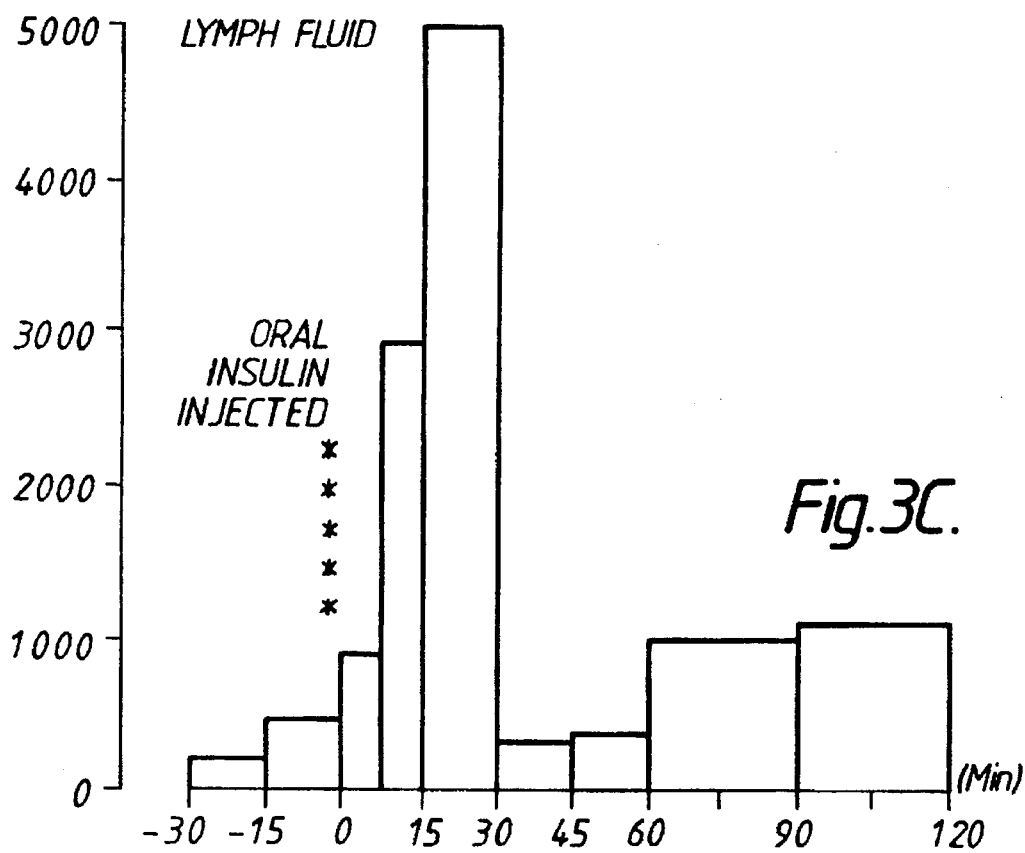
FIGS. 3A, 3B and 3C are bar charts of insulin levels in peripheral venous blood, hepatic portal blood and lymph fluid, respectively, against time, in Biological Example F.
Figure 3B:
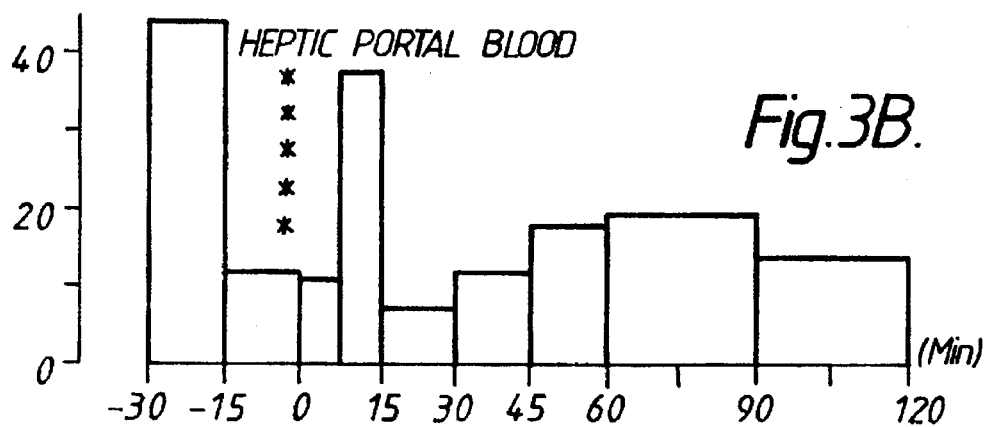
Figure 3A:
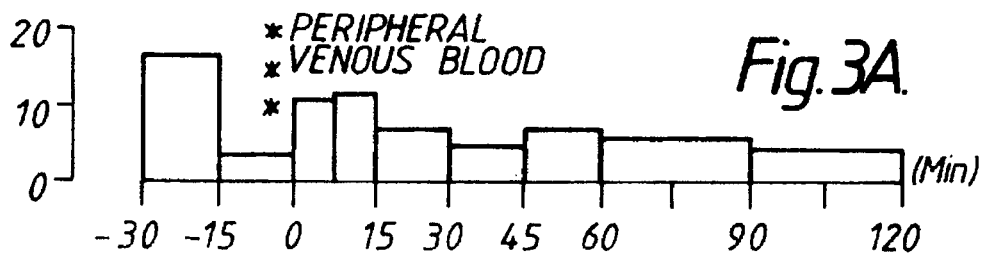

However, as can be seen in FIG. 3C a marked and sustained elevation of insulin in lymph fluid is observed and the level of changes range between 1,000 to 5,000 micro Units per ml of lymph fluid. The elevated insulin levels can not be accounted for by increased lymph flow, and must therefore be due to increased concentration.

Small hydrophilic, water-soluble chemicals such as sugar are known to be absorbed through the "pore system" of the intestinal membrane, carried into the capillary circulation and then into the hepatic portal vein in man. Lipids and lipophilic substances, on the other hand, are known to be absorbed via two distinctively different mechanisms. Those fatty acids having relatively shorter carbon-chains (for example $C_2$–$C_6$ or $C_8$ acids such as caproic and caprilic acid) are absorbed through the intestinal membrane with enzymatic and physiochemical 'assistance' from bile salts and pancreatic lipase. Ultimately, such absorbed lower-chained fatty acids are drained into the capillary blood and carried into the hepatic portal vein.

Those lipids and fatty acids having relatively longer chains, for example oleic acid and di-oleate and tri-oleate glycerides, as well as cholesterol and phospholipids, among other compounds, which form chylomicrons within the membrane, are absorbed through the intestinal membrane wall by mechanisms which may not as yet be clearly understood. Once in the intestinal membrane, they participate in the formation of chylomicra and are then 'sucked' into the villae of the intestinal system, drained into the lymph fluid, collected in the thoracic duct and ultimately dumped into the systemic circulation.

A marked and significant elevation of insulin found primarily in the duodenal lymph fluid in this study confirms that intra-duodenally administered insulin formulation (which is bound onto chylomicra or pro-chylomicra) is absorbed through the lymphatic system and not through the 'portal venous system'. The level of insulin recovered from the lymph fluid—up to 5,000 micro Units per ml—is so significant that it confirms that the insulin is absorbed by mediation of chylomicra and not through the portal system.

What is claimed is:

1. A pharmaceutical formulation consisting essentially of an emulsion having a hydrophilic phase and a continuous hydrophobic phase, wherein (A) the hydrophilic phase has a proteinaceous pharmaceutically active material and (B) the continuous hydrophobic phase consists essentially of the following components:

| | % (v/v) |
|---|---|
| cholesterol | 0.1–20 |
| phospholipid | 0.1–40 |
| lipophilic surfactant | 0.1–70 |
| unesterified fatty acid | 1–75 |
| cholesterol ester | 0–10 |
| apoprotein | 0–10, | wherein said lipophilic surfactant is selected from the group consisting of: glycerol esters; polyoxyethylated glycol monoethers; polyoxyethylated fatty acids; sorbitan fatty acid esters; polyoxyethylated sorbitan fatty esters; polyoxyethylated castor oils; poloxamers; and mixtures thereof.

2. A pharmaceutical formulation consisting essentially of an emulsion having a hydrophilic phase and a continuous hydrophobic phase, wherein (A) the hydrophilic phase has a proteinaceous pharmaceutically active material and (B) the continuous hydrophobic phase consists essentially of the following components:

|  | % (v/v) |
| --- | --- |
| cholesterol | 0.1–20 |
| phospholipid | 0.1–40 |
| lipophilic surfactant | 0.1–70 |
| unesterified fatty acid | 1–75 |
| cholesterol ester | 0–10 |
| apoprotein | 0–10, | wherein said lipophilic surfactant is selected from the group consisting of: glycerol esters; polyoxyethylated glycol monoethers; polyoxyethylated fatty acids; sorbitan fatty acid esters; polyoxyethylated sorbitan fatty esters; polyoxyethylated castor oils; poloxamers; and mixtures thereof; and wherein chylomicra comprising said components of the continuous hydrophobic phase are formed upon enteral administration of the formulation.

3. A pharmaceutical formulation consisting essentially of an emulsion having a hydrophilic phase and a continuous hydrophobic phase, wherein (A) the hydrophilic phase has a proteinaceous pharmaceutically active material and (B) the continuous hydrophobic phase consists essentially of the following components:

|  | % (v/v) |
| --- | --- |
| cholesterol | 0.1–5 |
| phospholipid | 0.1–40 |
| lipophilic surfactant | 0.1–70 |
| unesterified fatty acid | 1–75 |
| cholesterol ester | 0–10 |
| apoprotein | 0–10, | wherein said lipophilic surfactant is selected from the group consisting of: glycerol esters; polyoxyethylated glycol monoethers; polyoxyethylated fatty acids; sorbitan fatty acid esters; polyoxyethylated sorbitan fatty esters; polyoxyethylated castor oils; poloxamers; and mixtures thereof.

4. A pharmaceutical formulation consisting essentially of an emulsion having a hydrophilic phase and a continuous hydrophobic phase, wherein (A) the hydrophilic phase has a proteinaceous pharmaceutically active material and (B) the continuous hydrophobic phase consists essentially of the following components:

|  | % (v/v) |
| --- | --- |
| cholesterol | 0.1–5 |
| phospholipid | 0.1–40 |
| lipophilic surfactant | 0.1–70 |
| unesterified fatty acid | 1–75 |
| cholesterol ester | 0–10 |
| apoprotein | 0–10, | wherein said lipophilic surfactant is selected from the group consisting of: glycerol esters; polyoxyethylated glycol monoethers; polyoxyethylated fatty acids; sorbitan fatty acid esters; polyoxyethylated sorbitan fatty esters; polyoxyethylated castor oils; poloxamers; and mixtures thereof;
and wherein chylomicra comprising said components of the continuous hydrophobic phase are formed upon enteral administration of the formulation.

5. A composition as claimed in claim 1, wherein said hydrophilic phase further has water and a water miscible solvent in a ratio of from 0.5:1 to 2:1.

6. A formulation as claimed in 1, wherein said phospholipid is lecithin.

7. A formulation as claimed in claim 1, wherein said lipophilic surfactant is a long chain fatty acid, esterified as a glycerol ester.

8. A formulation as claimed in claim 1, wherein said continuous hydrophobic phase contains from 5 to 50% v/v of a hydrophobic phase miscible solvent.

9. A formulation as claimed in claim 1, further having from 0.1 to 50 g/l of a hydrophilic surfactant having an HLB value of at least 17.

10. A formulation as claimed in claim 9, wherein said hydrophilic surfactant is PEG-monostearate.

11. A formulation as claimed in claim 1, wherein said lipophilic surfactant has an HLB value of at most 10.

12. A formulation as claimed in claim 11, wherein said lipophilic surfactant is glycerol mono-oleate.

13. A pharmaceutical formulation consisting essentially of
(1) an emulsion having a hydrophilic phase and a continuous hydrophobic phase, wherein
    (A) the hydrophilic phase has a proteinaceous pharmaceutically active material and
    (B) the continuous hydrophobic phase consists essentially of the following components:

|  | % (v/v) |
| --- | --- |
| cholesterol | 0.1–20 |
| phospholipid | 0.1–40 |
| lipophilic surfactant | 0.1–70 |
| unesterified fatty acid | 1–75 |
| cholesterol ester | 0–10 |
| apoprotein | 0–10, | wherein said lipophilic surfactant is selected from the group consisting of glycerol esters, polyoxyethylated glycol monoethers, polyoxyethylated fatty acids, sorbitan fatty acid esters, polyoxyethylated sorbitan fatty esters, polyoxyethylated castor oils, poloxamers, and mixtures thereof, and (2) an ingredient selected from the group consisting of (a) up to 0.5% w/v of a protease inhibitor; (b) up to 10% w/v of an emulsification aid; (c) up to 10% w/v of a compound selected from the group consisting of dextrin, acacia, carboxypolymethylene and colloidal aluminum hydroxide; (d) up to 0.3% w/v of an antioxidant, and (e) up to about 3% of an antimicrobial agent.

14. A formulation as claimed in claim 1, wherein said continuous hydrophobic phase consists essentially of:

|  | % (v/v) |
| --- | --- |
| Cholesterol | 0.5–5 |
| Phospholipid | 0.5–10 |
| Lipophilic surfactant | 0.5–40 |
| Cholesterol ester | 0–5 |
| [Non-] Unesterified fatty acid | 1–50 |
| Apoprotein | 0–4. |

15. A formulation as claimed in claim 1, wherein said proteinaceous pharmaceutically active material is selected from the group consisting of insulin, interferon-gamma and interferon-beta.

16. A formulation as claimed in claim 1, wherein said pharmaceutically active material is insulin.

17. A formulation as claimed in claim 1, wherein said proteinaceous pharmaceutically active material is a hormone.

18. A formulation as claimed in claim 1, wherein said proteinaceous pharmaceutically active material is selected from the group consisting of calcitonin, growth hormone, erythropoietin, plasminogen activators, interferons, interleukins and blood factors.

19. A formulation as claimed in claim 1, wherein said proteinaceous pharmaceutically active material is selected from the group consisting of t-PA, urokinase, pro-urokinase and streptokinase.

20. A formulation as claimed in claim 1, wherein said proteinaceous pharmaceutically active material is selected from the group consisting of human interferon-alpha, IL-1, IL-2, IL-3, IL-4, IL-5, and factor VIII.

21. A formulation as claimed in claim 1, which is enterically protected.

22. A formulation as claimed in claim 1, which is in the form of a capsule.

23. A formulation as claimed in claim 21, which is in the form of a capsule.

24. A formulation as claimed in claim 22 or 23, wherein said capsule has a hard shell comprising gelatin.

25. A formulation as claimed in claim 24, wherein said hard gelatin shell is enterically protected by HPMC-P.

26. A formulation as claimed in claim 1, wherein said lipophilic surfactant is polysorbate 80.

27. A formulation as claimed in claim 1, wherein hydroxypropyl cellulose is present in said hydrophilic phase.

28. A method for the treatment or prophylaxis of a disorder controllable by a pharmaceutically active material, the method comprising administering to a subject the formulation of claim 1, wherein said formulation is administered orally or rectally.

29. A method as claimed in claim 28, wherein said pharmaceutically active material is insulin and said disorder is diabetes.

30. A method as claimed in claim 28, wherein said pharmaceutically active material is calcitonin and said disorder is selected from the group consisting of high bone turnover, acute hypercalcemia associated with malignancy, and osteoporosis.

31. A method as claimed in claim 28, wherein said pharmaceutically active material is calcitonin and said disorder is Paget's disease of the bone.

32. A method as claimed in claim 28, wherein said pharmaceutically active material is calcitonin and said disorder is osteoporosis.

33. A composition as claimed in claim 3, wherein said hydrophilic phase further has water and a water miscible solvent in a ratio of from 0.5:1 to 2:1.

34. A formulation as claimed in claim 3, wherein said phospholipid is lecithin.

35. A formulation as claimed in claim 3, wherein said lipophilic surfactant is a long chain fatty acid, esterified as a glycerol ester.

36. A formulation as claimed in claim 3, wherein said continuous hydrophobic phase contains from 5 to 50% v/v of a hydrophobic phase miscible solvent.

37. A formulation as claimed in claim 3, further having from 0.1 to 50 g/l of a hydrophilic surfactant having an HLB value of at least 17.

38. A formulation as claimed in claim 37, wherein said hydrophilic surfactant is PEG-monostearate.

39. A formulation as claimed in claim 3, wherein said lipophilic surfactant has an HLB value of at most 10.

40. A formulation as claimed in claim 39, wherein said lipophilic surfactant is glycerol mono-oleate.

41. A pharmaceutical formulation consisting essentially of
(1) an emulsion having a hydrophilic phase and a continuous hydrophobic phase, wherein
  (A) the hydrophilic phase has a proteinaceous pharmaceutically active material and
  (B) the continuous hydrophobic phase consists essentially of the following components:

|  | % (v/v) |
| --- | --- |
| cholesterol | 0.1–5 |
| phospholipid | 0.1–40 |
| lipophilic surfactant | 0.1–70 |
| unesterified fatty acid | 1–75 |
| cholesterol ester | 0–10 |
| apoprotein | 0–10, | wherein said lipophilic surfactant is selected from the group consisting of glycerol esters, polyoxyethylated glycol monoethers, polyoxyethylated fatty acids, sorbitan fatty acid esters, polyoxyethylated sorbitan fatty esters, polyoxyethylated castor oils, poloxamers, and mixtures thereof, and (2) an ingredient selected from the group consisting of (a) up to 0.5% w/v of a protease inhibitor, (b) up to 10% w/v of an emulsification aid, (c) up to 10% w/v of a compound selected from the group consisting of dextrin, acacia, carboxypolymethylene and colloidal aluminum hydroxide, (d) up to 0.3% w/v of an antioxidant, and (e) up to about 3% of an antimicrobial agent.

42. A formulation as claimed in claim 3, wherein said continuous hydrophobic phase consists essentially of:

|  | % (v/v) |
| --- | --- |
| Cholesterol | 0.5–5 |
| Phospholipid | 0.5–10 |
| Lipophilic surfactant | 0.5–40 |
| Cholesterol ester | 0–5 |
| Unesterified fatty acid | 1–50 |
| Apoprotein | 0–4. |

43. A formulation as claimed in claim 3, wherein said proteinaceous pharmaceutically active material is selected from the group consisting of insulin, interferon-gamma and interferon-beta.

44. A formulation as claimed in claim 3, wherein said pharmaceutically active material is insulin.

45. A formulation as claimed in claim 3, wherein said proteinaceous pharmaceutically active material is a hormone.

46. A formulation as claimed in claim 3, wherein said proteinaceous pharmaceutically active material is selected from the group consisting of calcitonin, growth hormone, erythropoietin, plasminogen activators, interferons, interleukins and blood factors.

47. A formulation as claimed in claim 3, wherein said proteinaceous pharmaceutically active material is selected from the group consisting of t-PA, urokinase, pro-urokinase and streptokinase.

48. A formulation as claimed in claim 3, wherein said proteinaceous pharmaceutically active material is selected from the group consisting of human interferon-alpha, IL-1, IL-2, IL-3, IL-4, IL-5, and factor VIII.

49. A formulation as claimed in claim 3, which is enterically protected.

50. A formulation as claimed in claim 3, which is in the form of a capsule.

51. A formulation as claimed in claim 49, which is in the form of a capsule.

52. A formulation as claimed in claim 50 or 51, wherein said capsule has a hard shell comprising gelatin.

53. A formulation as claimed in claim 52, wherein said hard gelatin shell is enterically protected by HPMC-P.

54. A formulation as claimed in claim 3, wherein said lipophilic surfactant is polysorbate 80.

55. A formulation as claimed in claim 3, wherein hydroxypropyl cellulose is present in said hydrophilic phase.

56. A method for the treatment or prophylaxis of a disorder controllable by a pharmaceutically active material, comprising administering to a subject the formulation of claim 3, wherein said formulation is administered orally or rectally.

57. A method as claimed in claim 56, wherein said pharmaceutically active material is insulin and said disorder is diabetes.

58. A method as claimed in claim 56, wherein said pharmaceutically active material is calcitonin and said disorder is selected from the group consisting of high bone turnover, acute hypercalcemia associated with malignancy, and osteoporosis.

59. A method as claimed in claim 56, wherein said pharmaceutically active material is calcitonin and said disorder is Paget's disease of the bone.

60. A method as claimed in claim 56, wherein said pharmaceutically active material is calcitonin and said disorder is osteoporosis.

* * * * *